(12) United States Patent
Rastelli et al.

(10) Patent No.: US 9,051,615 B2
(45) Date of Patent: Jun. 9, 2015

(54) METHOD OF DETECTING AND TREATING TUBEROUS SCLEROSIS COMPLEX ASSOCIATED DISORDERS

(75) Inventors: Luca Rastelli, Guilford, CT (US); Bonnie Gould-Rothberg, Guilford, CT (US); Ryan Murphey, West Haven, CT (US)

(73) Assignee: Celldex Therapeutics, Inc., Hampton, NJ (US)

( * ) Notice: Subject to any disclaimer, the term of this patent is extended or adjusted under 35 U.S.C. 154(b) by 25 days.

(21) Appl. No.: 13/462,300

(22) Filed: May 2, 2012

(65) Prior Publication Data
US 2012/0213778 A1 Aug. 23, 2012

Related U.S. Application Data

(63) Continuation of application No. 12/080,362, filed on Apr. 2, 2008, now abandoned, which is a continuation of application No. 10/991,173, filed on Nov. 16, 2004, now abandoned, which is a continuation of application No. 10/016,253, filed on Dec. 10, 2001, now abandoned.

(60) Provisional application No. 60/254,268, filed on Dec. 8, 2000.

(51) Int. Cl.
*C07K 16/18* (2006.01)
*C12Q 1/68* (2006.01)
*G01N 33/574* (2006.01)

(52) U.S. Cl.
CPC ............ *C12Q 1/6883* (2013.01); *G01N 33/574* (2013.01); *G01N 2500/10* (2013.01); *C12Q 2600/158* (2013.01)

(58) Field of Classification Search
CPC ........... C12Q 1/6883; C12Q 2600/158; G01N 33/574; G01N 2500/10
USPC ........... 530/350, 387.1, 387.3, 388.15, 388.2, 530/389.1, 387.9
See application file for complete search history.

(56) References Cited

U.S. PATENT DOCUMENTS

| | | | |
|---|---|---|---|
| 4,816,567 A | 3/1989 | Cabilly et al. | |
| 4,873,316 A | 10/1989 | Meade et al. | |
| 5,225,539 A | 7/1993 | Winter | |
| 5,871,697 A | 2/1999 | Rothberg et al. | |

FOREIGN PATENT DOCUMENTS

| | | |
|---|---|---|
| EP | 0125023 A1 | 11/1984 |
| EP | 0171496 A2 | 2/1986 |
| EP | 0173494 A2 | 3/1986 |
| EP | 0184187 A2 | 6/1986 |
| EP | 0264166 A1 | 4/1988 |
| WO | WO-8601533 A1 | 3/1986 |
| WO | WO-8809810 A1 | 12/1988 |
| WO | WO-8910134 A1 | 11/1989 |
| WO | WO-9518225 A1 | 7/1995 |
| WO | WO-9718454 A2 | 5/1997 |
| WO | WO-0061612 A2 | 10/2000 |
| WO | WO-0064941 A2 | 11/2000 |
| WO | WO-0208288 A2 | 1/2002 |
| WO | WO-0247534 A2 | 6/2002 |
| WO | WO-0262947 A2 | 8/2002 |
| WO | WO-0286122 A2 | 10/2002 |
| WO | WO-0286443 A2 | 10/2002 |

OTHER PUBLICATIONS

Shikano et al. (J. Biol. Chem. Mar. 16, 2001; 276 (11): 8125-34).*
Campbell (Monoclonal Antibody Technology, Laboratory Techniques in Biochemistry and Molecular Biology, 1984, Elsevier Science Publishers B.V.: Amsterdam, The Netherlands, vol. 13, pp. 1-32).*
Safadi et al. (J. Cell. Biochem. 2001; 84 (1): 12-26).*
Vaughan et al. (Nat. Biotechnol. Jun. 1998; 16 (6) 535-539).*
Gussow et al. (Methods in Enzymology. 1991; 203: 99-121).*
Kuan et al. (Clin. Cancer Res. Apr. 1, 2006; 12 (7 Pt 1): 1970-82).*
Weterman et al. (Int. J. Cancer. Jan. 3, 1995; 60 (1): 73-81).*
Arkin et al. "An Algorithm for Protein Engineering: Simulations of Recursive Ensemble Mutagenesis." *PNAS.* 89.16(1992):7811-7815.
Bandari et al. "Hematopoietic Growth Factor Inducible Neurokinin-1 Type: A Transmembrane Protein That is Similar to Neurokinin 1 Interacts with Substance." *Regul. Pept.* 111.1-3(2003):169-178.
Bergers et al. "Extrinsic Regulators of Epithelial Tumor Progression: Metalloproteinases." *Curr. Opin. Genet. Dev.* 10.1(2000):120-127.
Bächner et al. "mRNA Expression of the Murine Glycoprotein (Transmembrane) nmb (Gpnmb) Gene is Linked to the Developing Retinal Pigment Epithelium and Iris." *Brain Res. Gene Expr. Patterns.* 1.3-4(2002):159-165.
Carninci et al. "High-Efficiency Full-Length cDNA Cloning." *Methods Enzymol.* 303(1999):19-44.
Cheadle et al. "Molecular Genetic Advances in Tuberous Sclerosis." *Hum. Genet.* 107.2(2000):97-114.
Cole et al. "The EBV-Hybridoma Technique and its Application to Human Lung Cancer." *Monoclonal Antibodies and Cancer Therapy.* Reisfeld et al., eds. New York: Alan R. Liss, Inc. (1985):77-96.
Cote et al. "Generation of Human Monoclonal Antibodies Reactive with Cellular Antigens." *PNAS.* 80(1983):2026-2030.
Delagrave et al. "Recursive Ensemble Mutagenesis." *Prot. Eng.* 6.3(1993):327-331.
EMBL Accession No. AK089421, Dec. 19, 2002.

(Continued)

*Primary Examiner* — Stephen Rawlings
(74) *Attorney, Agent, or Firm* — Mintz Levin Cohn Ferris Glovsky and Popeo, P.C.; Shovon Ashraf

(57) ABSTRACT

Disclosed are methods of detecting and treating tuberous sclerosis complex associated disorders. Also disclosed are methods of identifying agents for treating tuberous sclerosis complex associated disorders.

5 Claims, No Drawings

(56) References Cited

OTHER PUBLICATIONS

Fang et al. "Identification of the Increased Expression of Monocyte Chemoattractant Protein-1, Cathepsin S, UPIX-1, and Other Genes in Dystrophin-Deficient Mouse Muscles by Suppression Subtractive Hybridization." *J. Cell. Biochem.* 79.1(2000):164-172.
GenBank Accession No. AJ251685, Jan. 28, 2003.
GenBank Accession No. AJ251685, Nov. 25, 1999.
GenBank Accession No. X00470, May 20, 1992.
Gura. "Systems for Identifying New Drugs are Often Faulty." *Science.* 278.5340(1997):1041-1042.
Hopp et al. "Prediction of Protein Antigenic Determinants from Amino Acid Sequences." *PNAS.* 78.6(1981):3824-3828.
Ike et al. "Solid Phase Synthesis of Polynucleotides. VIII. Synthesis of Mixed Oligodeoxyribonucleotides by the Phosphotriester Solid Phase Method." *Nucleic Acids Res.* 11.2(1983):477-488.
Itakura et al. "Expression in *Escherichia coli* of a Chemically Synthesized Gene for the Hormone Somatostatin." *Science.* 198.4321(1977):1056-1063.
Itakura et al. "Synthesis and Use of Synthetic Oligonucleotides." *Annu. Rev. Biochem.* 53(1984):323-356.
Kallow. "Pharmacogenetics and Personalised Medicine." *Fundam. Clin. Pharmacol.* 16.5(2002):337-342.
Köhler et al. "Continuous Cultures of Fused Cells Secreting Antibody of Predefined Specificity." *Nature.* 256(1975):495-497.
Kozbor et al. "The Production of Monoclonal Antibodies From Human Lymphocytes." *Immunol. Today.* 4.3(1983):72-79.
Kyte et al. "A Simple Method for Displaying the Hydropathic Character of a Protein." *J. Mol. Biol.* 157.1(1982):105-132.
Lendvay et al. "The Tuberous Sclerosis Complex and its Highly Variable Manifestations." *J. Urol.* 169.5(2003):1635-1642.
Liu et al. "Chimeric Mouse-Human IgG1 Antibody that can Mediate Lysis of Cancer Cells." *PNAS.* 84.10(1987):3439-3443.
Mancinelli et al. "Pharmacogenomics: the Promise of Personalized Medicine." *AAPS PharmSci.* 2.1(2000):E4.
Melrose et al. "A Solid Phase Enzyme Linked Immunofiltration Assay for Secretory Leucocyte Proteinase Inhibitor." *Clin. Chim. Acta.* 225.1(1994):17-28.
Narang. "DNA Synthesis." *Tetrahedron.* 39.1(1983):3-22.
Pollack et al. "Treatment Parameters Modulating Regression of Human Melanoma Xenografts by an Antibody-Drug Conjugate (Cr011-voMMAE) Targeting GPNMB." *Cancer Chemother. Pharmacol.* 60.3(2007):423-435.
Rasool et al. "Secretory Leukocyte Protease Inhibitor Antagonizes Paclitaxel in Ovarian Cancer Cells." *Clin. Cancer Res.* 16.2(2010):600-609.
Rininger et al. "Differential Gene Expression Technologies for Identifying Surrogate Markers of Drug Efficacy and Toxicity." *Drug Discov. Today.* 5.12(2000):560-568.
Selim et al. "Anti-Osteoactivin Antibody Inhibits Osteoblast Differentiation and Function in vitro." *Crit. Rev. Eukaryot. Gene Expr.* 13.2-4(2003):265-275.
Shimkets et al. "Gene Expression Analysis by Transcript Profiling Coupled to a Gene Database Query." *Nat. Biotechnol.* 17.8(1999):798-803.
Stefănescu et al. "Anti-Phosphotyrosine and Anti-Phosphoserine Antibodies in SLE Sera." *Roum. Arch. Microbiol. Immunol.* 50.3(1991):193-197.
Tse et al. "CR011, a Fully Human Monoclonal Antibody-Auristatin E Conjugate, for the Treatment of Melanoma." *Clin. Cancer Res.* 12.4(2006):1373-1382.
UniProtKB/SWISS-PROT Accession No. Q99P91, Mar. 15, 2005.
Weintraub et al. "Anti-Sense RNA as a Molecular Tool for Genetic Analysis." *Trends Genet.* 1(1985):22-25.

* cited by examiner

SEQUENCE LISTING

<160> NUMBER OF SEQ ID NOS: 27

<210> SEQ ID NO 1
<211> LENGTH: 2520
<212> TYPE: DNA
<213> ORGANISM: Homo sapiens

<400> SEQUENCE: 1

```
ggctctggct cgggctcggg ctggggctgg ggcttgggct ccagctcggg ccctgcacct      60
gtgactcggc ggcgttgctc ctccgctgcc ccatggcccc gtcccggctg cagctcggcc     120
tccgcgccgc ctactccggc ttcagctcgg tagccggctt ctccatcttc ttcgtctgga     180
cggtggtcta ccgacaaccg gggactgcgg cgatgggggg tctcgcaggt gtcctggcac     240
tgtgggtctt ggtgactcac gtgatgtaca tgcaggatta ctggaggacc tggctcagag     300
ggctgcgcgg cttcttcttc gtgggtgctc tcttctcggc agtctccgtt tccgccttct     360
gcaccttcct ggcattggcc atcacccagc atcagagtct caaagacccg aacagctact     420
acctctcctg tgtctggagc ttcatttcct tcaagtgggc cttcctactt agcctctacg     480
cccaccgcta ccgggctgac tttgcggaca tcagcatcct tagtgatttc taacccaggg     540
aatgaggtca ccacagcctg ggggccctcg ggatctggac tcagcttccg agtcagcaag     600
ggagctcacc ccaaccctg gggaactcca gaaccatggc agagtatatg ggcccgttca     660
gtttctcaga aatctgtctg gtcccctttt ggggaagata tagagctgtt aaagggatac     720
tgccaatctg cccaatctgc ccgttagccc agctagaggg cagcttagac cttccaaat      780 agatctattt tcttagccct ctgagggatc tctgtaagta gggccacgac aatgaattca     840
atgggtagga ttggaactat ggctagtgac aggggctggg acaggcttcc ttgctacccc     900
agacttcatt gaagctgtgt gtggggggagg catcaaaggt ctggtcaaga gaggaatctt     960
tagtacagat ctccatcccc tgttccccac cctgttaccc tgaagtgtcg ggtagccaaa    1020
ctcaccggtc cttagggaat tgacaattgg ctccttccct aagcagcaca gttggacaga    1080
atccagcgtc cgtccgtcct accttcccat ccagagtttg tttcccatga gggtgctagc    1140
gccagccaac cattcccatg tgtcgcatat gcacacatga ccacacacac cagagcagga    1200
ctcctcggat gaggctagac ttgaggacca caggaaacac acccctgcac ttagaagggc    1260
tttgggatcg ggggcaacct ggtgggggca agtgggagct ctccatctgt actgagtctc    1320
caaccttgcc cctcactgca caagaccacc ctgaccgtga ggacctcctc cctgcaccag    1380
atcctaactc tgacctttca ccttctctct ctcctgaagg aactcttctg agtggacatg    1440
ggcccaaggc cttacctaag cggagaggga gggcagggc tgctactctt ctctgtaacc    1500
ttctctgatg ggttgtcact ttgcacgtct actcttccac ttgggcactg cccccagctc    1560
tctgccttac ctgtgttatg ggcacttaag cagaaataca gcggccattt taaccagcaa    1620
aaaaaaaaaa aaataggggg gtgggcggtt ttgagagggg acaagagtgg gcaagatggg    1680
ggctctagct gtctgatcat ctccctaagt ttggggctac tagacggtat tcctcatctc    1740 tggtcccta tgggagacca ccagctgaga tctcctttgc tctcccagtt ctgtcccagc    1800
```

```
cagggttagg atgcccacag actcaacatc cctgcagatt ccatctcccc accctaagcc    1860
aaggtagatg ggaaagggaa tctttctttt tctacccag ccagactact tggggctcca    1920
agttgaccag gatgtgtgga ttcagaagca gaaaggcagg agctagcacc tctctcacgc    1980
tgggtacact tgtcctggcc tgtgtttgcc tcaccctggc ctttacagtg taaaaacacc    2040
atgggacttt agagcaggga aggataagga acagtgtcac ttctagagcc ttctgctggt    2100
agacgctcct actgatagag gaggtaaaga ctactgacct cccggctagg cctggcttaa    2160
gccaggcgtg gcctgcgtca aaccttttg cggtgtctta gcaacctgaa cctgagatct    2220
tattcccgaa tcccacaggg cccaatgtgc agggctcagc ctggggccat ctcccttttc    2280
acctgggttg gtgagcatgt atttggagtg gtttcttcct gcatgtatta gccaaggaag    2340
gacaagggac tagagggtct gagttaggtc cagacttgtc cccttttcccc agcccatcac    2400 aggatgctgg gtgcacaccc actccactga cgatgtccca ccaacatcca ggaggcgttc    2460
tcccaaggac tttaaagcaa ataaaacata tattgttcag aaaaaaaaaa aaaaaaaaa    2520

<210> SEQ ID NO 2
<211> LENGTH: 1860
<212> TYPE: DNA
<213> ORGANISM: Homo sapiens

<400> SEQUENCE: 2
aagcgtgacc ctaagtctag cctggagcca gggctagagt ggtcatttct ttgtggggtg      60
ctgccaggga ggggccagac ccacaggcta ctcaaagggc ctagagaccc ctccccaggc     120
aggtgctgcc ccaggaggag catgtcctgg ggtccgggga ctgaagtcca tgtggcctca     180
gccccccaca cccagaacac cgcttgccta aggtgctttt ggctttagtg tgtgatgttt     240
gctgtgcttc tgggctgaat tagcttccaa atcaggacct ggagcctcta ccctggccca     300
gccagccagt gtgagctctg gtctgtgaga tgggcagcta cgggcagtg gagcagcatg      360 tggtgggagg ggcaaggctg ggacccagtg gtttacagac ctgtggccct cctggagcaa     420
cctggcagct acggatccca gaaccccctg ggcttcagct cccccagagg ggagaggctc     480
cacgttgctt tccttcccca aaatcccttt ctttgtgctg gtgtctggga ccaaaaggag     540
tgggcagagg actcggaggg cctaggggtc ccagtcgggg catctgtagc tcctaagcac     600
gacaagcatc agtgcagggg accctggcct tgactccaac tggcctggcg ccaggaacct     660
ccagggccag agcagcccag ctgcagccag cctgcccact atgggtatgt tcctggccta     720
aggtccggag ggaggtttgg ggtatccctg cctgggtgcc tgggtgtgcc ctggggcctc     780
tcagaagcac aaatgctgcc ccctggccgt gagcaggcca aaggtgaat gtatatagca     840 tgagaggcgg gcactgccca gacgtggctg tgaacttgtg ctgtctcggg agtcctgacc     900
ttctgtgcgt gagtgccccc atctgtgacg tttcactcac cgaggctgaa gaaaggaagc     960 agggaaatg aaagcagggg tttctcgccc tgacccctgc ggaggagacg gctcctacca    1020
ctgcggttgg cttcatttcg ttttcctgat ttctggggtg ccacttacct actcaatccc    1080
agtggtccac ccccacatcc ccagggagtg agcagtccag tgccagctgc ctgtgattgg    1140
tccccagtcc ctattaccca aggggaccct acagctctgg tgggtaacaa ggagggctaa    1200
gccaccaaac cagagcccga tcccttgccg agccaggagg agggatctgg ctgagaaaac    1260
tgataggact ggaggccccc accccaacca acactctctg gtttatgtga gtagcagaag    1320
atcccggcct ggagcatcct tcaagccctt ctccctgtgc ccaccccgcc ccccccccc     1380
```

```
cccatatcac tatgcaattc ttgacccag ctccaaagct tgccctaccc ggtcccagct    1440
ctgtccggcc cagaaggtgg ctagctggtg ggcacaggt gaccagggtc tctttgtttt    1500
tcatcacagc ggtggtgtgc cgcacccttc ctcccatatg tgattttgtg agattgcctc    1560
ccagttacgg tccctctgcc tgcatctgcc cccagtggac tatgtcatct gaatcgagcc    1620
agccccaagt tcccctccag cctctgtagg gccatggctg tgtgttactg ttgctgtgct    1680 ttcattttt aaactgggtt tggggtttga ttttattc tgtggggaac tttattttc      1740 ttggcaaata actaaagttc ttgtccatgt aatttctgtg gtctctattc agcttgggtt   1800
tcatgtttta aaataaacaa ttttaagaaa caaaaaaaaa aaaaaaaaa aaaaaaagc    1860

<210> SEQ ID NO 3
<211> LENGTH: 750
<212> TYPE: DNA
<213> ORGANISM: Homo sapiens

<400> SEQUENCE: 3
cttgtttatc ctactcgggt agtttcctac taatttcaag actagtgtta acattctaag      60
gtagttatct tagggtagat tcaaggtttt agatgactaa cagttcagat tttctgatca     120 atttttaaa cactagagaa taaaagtgta ctagagaata aaagcagctt catagttaat      180
tctcaccaat tggccctttg ctagctgctg gctttaggta cataggat aatatgtgtc      240 cacgtttcta cttggaactg gtaaaagttg tcactggctg gaaaatggta tctctctctt     300
gtatacaaga tggtccattg acactggtac tttatgaagc agttctttgt ttgtttgatt     360
gagctctctt gaaccttgtt catcttttag ttttgcttg gaatggaatg gaactggttt     420
gaagttaaag gaaatattca ttttgaaact tgttcatttt gaaggaaat gcaagtttca     480 aaatgaaaaa taaaatgaaa aaggaaataa attattgtcc cagatggtca cttgagtttt     540 aaaaatggc tgcacacagt aaactgcta aaacaaaaa cttacctcat tattggtttg      600 catcttttt cagctactaa ttttatacca aaatgttaaa tatttatatt gtttgagttt     660
caatcttgta tggaaaaaa taattagtag gtctaaaat gccatgcttt ccaataaaga     720
agttaaaaaa atcatcagta atgtgaattt                                    750

<210> SEQ ID NO 4
<211> LENGTH: 281
<212> TYPE: DNA
<213> ORGANISM: Homo sapiens

<400> SEQUENCE: 4
gggcccctcc gtctcagagc aactataccc tctacctcgg aaggagcagc agagagagaa     60
gccacaggcc accaggaggc ccagcaaagc caccaactat ggaagcttct cagccacccc    120
acctcccacc ctctgggagg tcagcacaag agttgtgggc acaagccgtt tccgggacaa    180
ccggacagac aaacgggaac atggccatca ggacccaaat gtggtgccag gtcctcacaa    240
gccagtaaag gggaagctgc ccaaaaagaa ggacagaatt c                       281

<210> SEQ ID NO 5
<211> LENGTH: 1568
<212> TYPE: DNA
<213> ORGANISM: Homo sapiens

<400> SEQUENCE: 5
cgcgcgggag ccaagatgcc tcgcggggac tcggagcagg tgcgctactg cgcgcgcttc     60
tcctatcttt ggctcaagtt ctctctcatc atctactcca ccgtgttctg gctgattggg    120
```

```
ggcctggtcc tgtcagtggg gatctacgca gaggcagagc ggcagaaata caaaaccctg    180
gaagagtgcc ttcctggccc ccgccatcat cctcatcctc ctgggggtgg tcatgttcat    240
cgtctccttc atcggggtgc tggcttccct ccgggacaac ctgtgccttc tgcagtcgtt    300
tatgtatatc ctggggatct gcctggtcat ggagcttatt ggtgggtctg tatttagggg    360
ccgccggaac cagactattg actttctgaa cgacaacatc cggagaggaa tcgagaatta    420
ctacgatgat ctggacttca gaacatcat ggactttgtt cagaagaagt tcaagtgctg     480
tggcggggag gactacagag actggagcaa aaaccagtac catgactgca cgccccccgg    540 gccctggct gacggggttc cctacacctg ctgcatcagg aacacgatgt tgtcaacacc     600
atgtgtggct acaaaacaat cgacaaggag cgcctgaatg cacagaacat cattcacgtg    660
cggggctgca ccaacgccgt gttgatatgg ttcatggaca actataccat catggcgggc    720
cttttactgg gcatcctgct tcctcagttt cttggtgtgc tgctgaccct actgtacatc    780
acccgtgtgg aggacattat cttggagcac tctgtcacgg atggattgct gggacctggt    840
gccaagtcca aacggacac agcaggcact ggatgctgcc tgtgctatcc cgattagcta     900
tgctgattga gctatcctgg cccggcacag cagctcccag ccggactgta ctgcaaagtg    960
catctaagac tacacaagct ggacaggacc agctgcagct cctctgccca cccacggcgc   1020
tgaccaaagc ccagggtgta tgtacctgcg tatagtgtct gatggccact cctcctaggg   1080
gaaagctgaa ccctgtggga tcccgggaac agggatagcc cagctccggt tctgagtcct   1140
ggagaaggca gctcagggct ccgtgtgggc tcttttcctt tctggcagtg ccttggccag   1200
tggtcattat gccccttcaa gggcagtttt gcagtgatta ttttaaaggc aagaaggga    1260 gtgtatctgt tctataggga agtcctgggt gcagccctgg tacactactc tagatgtgac   1320
gttggactgt gtctcaaatt cccaggtgcc ttgagtcctc tgtaaggctc ctgctttgcc   1380
cacccatttt ctacatatgt ttttttttctt tttttttttt aataaccgtg ttttgtatac   1440
aattaacaag agtttctggc tattcaaaac tagccacccc tgaccgagtc cactcacccc   1500
tccccgttag ttcattaatt gaacaataaa tatgtgtttt ggggggtggt ctttaaaaaa   1560
aaaaaaaa                                                             1568

<210> SEQ ID NO 6
<211> LENGTH: 300
<212> TYPE: DNA
<213> ORGANISM: Homo sapiens

<400> SEQUENCE: 6
gccggctctt tgtggaggac tccatccatg accagtttgt gcagaaagtg gtggaggaag     60
tagggaagat gaaaatcggc gacccctgg acagggatac caaccatggc ccgcagaacc    120
atgaggccca cctgaggaag ctggtggagt attgccaacg tggtgtgaag gaaggggcca   180
cactggtctg tggtgggaac caagtcccaa ggccaggctt cttctttcag ccaaccgttt   240
tcacagacgt ggaggaccac atgtacatcg ctaaggagga gtccttcggg cccatcatga   300

<210> SEQ ID NO 7
<211> LENGTH: 965
<212> TYPE: DNA
<213> ORGANISM: Homo sapiens

<400> SEQUENCE: 7
cccacagctc ctgcccactc accaggtcca ggggagagca ggcggtgact cgatgacaag     60
```

| | |
|---|---|
| tgcctttagt tgaagagcac atctcactca ttcctctctc agtacctgat acattcctct | 120 |
| gtgctaaccc ccccttgggg aggacccacc ctctggaggc tggacttggg gcgaacaggc | 180 |
| actcacctgt cactgccaag ggcgggcagg ccatccttcc gagcccatgg gagccgggac | 240 |
| cactaagact gctggtggga agaagttggg tgctgggctg atggtcttgc tttctcttgg | 300 |
| tcttcgcttg taatgtggct ggcccatgtt ggttttatgt ttaatgctgt gcttataata | 360 |
| agaaagagcc cccccaagct gtacatttat aaaaagtgat catatactgt atatagaaaa | 420 |
| atctagaagc acatatgaat gcagcaggta gtattccact gtacccattc atgaaggtag | 480 |
| gttttattac aggactcgca ccaggtactt acagacgcgc cctctcctct ttgcctagag | 540 |
| aaacagtcac tgcattcccg cacagtccct cagacccct accctcttc cctgtaggaa | 600 |
| attctcctgt gacccctctg ccgtcctccc ttacttccta aataaatgta acggagtcag | 660 |
| tgcaaaaaaa aaaaataaa tgacatttat tgtgggttat aattttctcc taaaaacaaa | 720 |
| accagtggta tggtcatacc caccattgtt tccccacttt ccatgaccgt cacaaacatc | 780 |
| tgggatgagc accttgtgag caggaaaagt tatgctttaa gaaatttctg gccaggcgtg | 840 |
| gtggcataca cctttaatcc cagcactcgg gaggcagagg caggtggatt tctgagttcg | 900 |
| aggccagcct ggtctacaaa gtgagttcca ggacagccag ggctacacag agaaaccctg | 960 |
| tctcg | 965 |

<210> SEQ ID NO 8
<211> LENGTH: 408
<212> TYPE: DNA
<213> ORGANISM: Homo sapiens

<400> SEQUENCE: 8

| | |
|---|---|
| gccgggtctg aaaaggacta ggctggcatt ggtgacaccg agcttgttgg cagccacaca | 60 |
| ggtatagttg ccatagtgtt cctcagtgac attggtcacc gtcagggagg actggccctc | 120 |
| agtgctctta atctcaaggc catttgcact gtttatcctg tgtcatccc ggtaccactc | 180 |
| aaagtcaggt gcaggcaccg ctgaggcttc acatttgagg gaagcttgtc gtcctgtggt | 240 |
| ggcttcgttg ctcttcgact ccgtgatagt gggtggatag ttcacagtga ccttgacttg | 300 |
| tttgacatcc gccgaggaga cctcgttggc agccttgcac tcatatttgc ctgactgttc | 360 |
| cctggtgatg cctaggatct ccagatattc ttcttctcct tcaaatty | 408 |

<210> SEQ ID NO 9
<211> LENGTH: 355
<212> TYPE: DNA
<213> ORGANISM: Homo sapiens

<400> SEQUENCE: 9

| | |
|---|---|
| gtgcaccaga tgttctacga ggccctagat aagtacggga acctcagtgc tctgggcttc | 60 |
| aagcgcaagg acaagtggga gcgtatctct tactgccagt actacctgat tgcacgcaaa | 120 |
| gtagccaaag gcttcttgaa gctcggccta gagcgtgccc acagcgtggc gatccttggc | 180 |
| ttcaactctc cagaatggtt cttctctgca gtgggcacag tgttcgcagg gggcattgtc | 240 |
| actggcatct acaccaccag ctccccggag gcctgccagt acatctctca tgactgccga | 300 |
| gccaatgtca tcgtggttga cacacagaag cagctggaaa agatcctgaa gatct | 355 |

<210> SEQ ID NO 10
<211> LENGTH: 918
<212> TYPE: DNA
<213> ORGANISM: Homo sapiens

<400> SEQUENCE: 10

```
cggatcatct gggtcgcgac cttgaggccg ggaatcgagt ttccaaacgt gcggggggcct      60
tcgccggctc tgctgccccc tttctctcca tggcagcggc ccggaacctg cgcaccgcgt     120
catattcgga ggcttcatct ccatggtcgg cgccgccttc tatcccatct acttccggcc     180
ccttatgcgg ctggaggaat accagaagga gcaggctgta aatcgagctg gtattgtcca     240
ggaagatgtg caaccgccag gttgaaagtg tggtctgatc catttggcag gaaatgaggc     300
tgtcagcaag tctgatgagg aaagtggacg tctttatcct gtgcactccg cagtggggac     360
aatagatgcc tcactgtggc agcatggcat ggagagggaa ctctcatgct gctagccaga     420
ccccttgtga tagagactgt gtgcaaagac agtgcttccc ttaactccct ggagaacctg     480
aacagatgcc accattagga agtgccttgc ggctccattg actttgcagg agcagagcca     540
gcctgcaagg ctgtttgtgg aagatctgct gctcctgcag tctttatcac ttccaagctg     600
tgatgtgaac acaagcaacc tgtgggctca aggtccgtgg ctgctctgac accttttgaa     660
taagcgattt cagtgcaaat ggccttgcca agctgcctcg cagggttctt ggaggatgtt     720
tcagttgata aaactgtttg aagacaggat ccttggcact gtttaagaat atacactgct     780
cagcttaacc atttcattga aagtcactgt gtgtggaagt gaatagggag cgagtcacac     840
tagactatac cacacacagt agattcctgc gtgaggctgc aggtattaaa atggtttctc     900
ttaaaaaaaa aaaaaaaa                                                   918
```

<210> SEQ ID NO 11
<211> LENGTH: 1113
<212> TYPE: DNA
<213> ORGANISM: Homo sapiens

<400> SEQUENCE: 11

```
ggagacccaa gatctgaacc agccagccag gtgctgcaca gcctcaactt tgggagcaga      60
ggccctgtgg ggttaacttg ggtctgccag aaacagtgct tcccgcaggg aaaatcttgg     120
gtcaagatgg aggctgctct ggaacactga gtgtttcaag ggagaaagag tgggaaccgt     180
ggccctttgg ggccagaccc tgcaggagct tgcctcgcct tgaggagga ggcactgctc     240
ttcaggtgcc ctggagggggc ttttagtgcc atccccacag cagagtaaag gtggcgcgta     300
tgtcatcggg tggcttgcg ctggtagaac gctgttctct accctgctgc agcctttcac     360
actcacacac acccaaacac acacttctcg gccctgtatg ttcaggtgag agacaaggga     420
agatggctca tcattttcag ccatgtcccc aaagtggcct ctctttcatg ctctgtgggc     480
tttggcctgc agctgttcca gagttaggga tgtgattttt gtctgtgagg taccccttgc     540
cctagtggat cagttacagg cctatgtcca gcaccagagt ccctgttccg atatcatcac     600
agatagcctg ttgttttcca cagaggagcc agatgtaagt cagacacctc agcctacca     660
gtctcctgcc atcagctttg gctctaatgg gctcttggtg gcctccttgg tgtgtcactg     720
gtacaggaca gcaagtggct cagaaaggct gcttgctcct gagctcagcc acttattcac     780
atggttcaga gcagatcttt gtactcttca gactcaagta tggtgatctg tttgacagta     840
gaggtctggc ctaccctca ccctcattct ccagcacctc taacaagaac cacactcatg     900
cctctggtgt cagttttctt gtctgccttc cctggcctac ctagatattt atttcttgtg     960
ttttatgaat agttaagccc tgcccatctg tgccttcag acggaaacac agaaacctag    1020
gctgtgccat ttgtcttctc acagttgttt aatgaaacct caaggaatat ggaaataaag    1080
```
cctagaccct ggagtggtga aagagtaaaa aaa                                  1113

<210> SEQ ID NO 12
<211> LENGTH: 594
<212> TYPE: DNA
<213> ORGANISM: Homo sapiens

<400> SEQUENCE: 12
agatctctgt ttcctctttc ttctctcctc tatgctcttc tgtagcctac cctcagggtg      60
atctctaacc caaactaatc ccgaggaaca gacacttggc tcagctccac ctactacctg     120
gctcacctgt tcccagaatc tccatagaag agggcacttt cttctcaag ttaccctaac      180
attctctgca ggataaaatc atgagtccag cctgtctgtg gaactggggc ctgtctgcag     240
cttccctgca gaagtgtcca ttcactttgg gtgatcttcc cgaccaagat acttaggtgt     300
tttggccagc accagtattt ctatgaattc ctgatctgga gttgaataga caggaatcaa     360
gacctaggct tttcactgtg tgaacctgag catgtggcct gacctgctgg aagctcctct     420
gctcttgtgt gaagcaggaa tgctgtcagg cacacagcac aacacaccag tggtggagaa     480
cgctaatccc aacacacaaa ttccacagaa atggcactat cctcgggtct cctgcctaac     540
catggacaaa gctgagaata aacagtgctt tactttgaaa aaaaaaaaaa aaaa           594

<210> SEQ ID NO 13
<211> LENGTH: 713
<212> TYPE: DNA
<213> ORGANISM: Homo sapiens

<400> SEQUENCE: 13
caattgtttt ttctaaccat cttagggaac aatacattgc ataattgat aatagtgcca       60
tcactgtaat aaactttaga gacttttttt aatgtaaaag ttgttggtca ccttgtttcc     120
tgtaaccttc actctgtcac acgagttggc tcataggttg tgtttgtcta tcagaaataa     180
gaaaaacaca agtgaagaaa atgttggcat gaagtcatcc atctgcaatg aaaaacctaa     240
aagactacgg gtcactcatg ttatcaatat aatttataat cctgttcagt gtacaaaatt     300
gtgggttttg tactcaccca aaagactaaa acaccagttt ttcttacagt atctatctac     360
agagcttatt ctcccctatt atttgggaaa ctctgagact ccatattgca gaagtcaagg     420
aataggccat ataagaaaat gtagcttgtt tttattattt ctgcatattt atttctagat     480
cttgggctca tttgttaaca gaataagttg tcaaaggtaa agtccttgag tctgggaatg     540
agccatcgtt ccaaaaccaa cacaccctgt gtggaaattt tacttgactc tgttttgctg     600
catagaattc agtgtctctt ggccattccc cctcattcct atactaaatt cttttgaagac    660
actggtaaca gtttgtggta gactacagtt gaaaaaactc aatccttatt tct            713

<210> SEQ ID NO 14
<211> LENGTH: 306
<212> TYPE: DNA
<213> ORGANISM: Homo sapiens

<400> SEQUENCE: 14
ggatccctcc accctatgac aagaaaaagc ggatggtggt ccctgctgct ctcaagggtt      60
gttcgcgctg aagcctacca gaaagtttgc ttacctgggg cgtctggcgc atgaggtcgg     120
gtggaagtac caggcagtga cagccactct ggaggagaaa cggaaggaaa aggccaagat     180
gcactatcgg aagaagaagc agatcttgag gttacgaaa caggcagaaa agaatgtgga     240
gaagaaaatc tgcaagttca cagaggtcct caagaccaac ggactcctgg tgtgaaccca     300
ataaag 306

<210> SEQ ID NO 15
<211> LENGTH: 66
<212> TYPE: DNA
<213> ORGANISM: Homo sapiens

<400> SEQUENCE: 15

| | |
|---|---|
| gaattcgaat cacgctcacc agccgcaacg tgaagtcgct ggagaaggtt tgtgcggact | 60 |
| tgatca | 66 |

<210> SEQ ID NO 16
<211> LENGTH: 1613
<212> TYPE: DNA
<213> ORGANISM: Homo sapiens

<400> SEQUENCE: 16

| | |
|---|---|
| ccagctcaga ggttctaggg gcagccggcg cgcttctcta gttgcagctt gggcggctcc | 60 |
| tgtggtgggc ggctaggggc gagccgggat gggctataga cgcgcgacgt gatcagttcg | 120 |
| cacgcggacc cacgcctccc atcgctctgc ctcaagagcc tattctgtgg gtgcaggcac | 180 |
| gcaccggacg cagacccggc cggagcatgc ggggtgcggt gtgggcggcc cggaggcgcg | 240 |
| cggggcagca gtggcctcgg tccccggggcc ctgggccggg tccgccccccg ccgccaccgc | 300 |
| tgctgttgct gctactactg ctgctgggcg gcgcgagcgc tcagtactcc agcgacctgt | 360 |
| gcagctggaa ggggagtggg ctcacccgag aggcacgcag caaggaggtg gagcaggtgt | 420 |
| acctgcgctg ctccgcaggc tctgtggagt ggatgtaccc aactggggcg ctcattgtta | 480 |
| actacgggcc caacaccttc tcacctgccc agaacttgac tgtgtgcatc aagcctttca | 540 |
| ggcactcctc tggagccaat atttatttgg aaaaaactgg agaactaaga ctgttggtgc | 600 |
| gggacatcag aggtgagcct ggccaagtgc agtgcttcag cctggagcag ggaggcttat | 660 |
| ttgtggaggc gacaccccaa caggacatca gcagaaggac cacaggcttc cagtatgagc | 720 |
| tgatgagtgg gcagaggggga ctggacctgc acgtgctgtc tgcccccctgt cggccttgca | 780 |
| gtgacactga ggtcctcctt gccatctgta ccagtgactt tgttgtccga ggcttcattg | 840 |
| aggacgtcac acatgtacca gaacagcaag tgtcagtcat ctacctgcgg gtgaacaggc | 900 |
| ttcacaggca aagagcagg gtcttccagc cagctcctga ggacagtggc cactggctgg | 960 |
| gccatgtcac aacactgctg cagtgtggag tacgaccagg gcatgggaa ttcctcttca | 1020 |
| ctggacatgt gcactttggg gaggcacaac ttggatgtgc cccacgcttt agtgactttc | 1080 |
| aaaggatgta caggaaagca gaagaaatgg gcataaaccc ctgtgaaatc aatatggagt | 1140 |
| gacttgcagg gtgacacagt actgttgtcc ttcagatgag ccatgtttg tgggctcagt | 1200 |
| cgctctatca tatcctgata gagattgcag actggtggca tgggcccagc ctggtgctag | 1260 |
| aactgggaag gtcatgctg ttctgacccc ttaggtccca gccaaggatg ccctgaccca | 1320 |
| ttggaactgc tgtaaaatgc aaactaagtt attatatttt ttttgtaaaa gaaaaaaaaa | 1380 |
| aaaaaaaaag aaaactccgc gcacaggggg ggtacgtccc aattcgccaa aaacagatgc | 1440 |
| tagaaccct ggcggccccc ccaccccac gggagacact agctaaccaa ttaatgcttg | 1500 |
| gaaaatccct tctgcaccgg tagtacgaaa ggcccacgat gccttcaaag ctgcctggac | 1560 |
| ggaatgcaaa tgaacgctaa tttctaatcc ggtaattgta accgcattct aca | 1613 |

<210> SEQ ID NO 17

<211> LENGTH: 2245
<212> TYPE: DNA
<213> ORGANISM: Homo sapiens

<400> SEQUENCE: 17

```
acgtgaccgt gagaccctag gagcaatggc ggggcggctg gctggcttcc tgatgttgct      60
ggggctcgcg tcgcaggggc ccgcgccggc atgtgccggg aagatgaagg tggtggagga     120
gcctaacaca ttcgggctga ataacccgtt cttgccccag gcaagccgcc ttcagcccaa     180
gagagagcct tcagctgtat ccgggcccct gcatctcttc agacttgctg gcaagtgctt     240
tagcctagtg gagtccacgt acaagtatga attctgccct ttccacaacg tcacccagca     300
cgagcagacc ttccgctgga atgcctacag cgggatcctt ggcatctggc atgagtggga     360
aatcatcaac aataccttca agggcatgtg gatgactgat ggggactcct gccactcccg     420
gagccggcag agcaaggtgg agctcacctg tggaaagatc aaccgactgg cccacgtgtc     480
tgagccaagc acctgtgtct atgcattgac attcgagacc cctcttgttt gccatcccca     540
ctctttgtta gtgtatccaa ctctgtcaga ggccctgcag cagcgctggg accaggtgga     600
acaggacctg gcagatgaac tgatcacacc acagggctat gagaagttgc taagggtact     660
ttttcgagga tgccggctac ttaaaggtcc aggagaaaac ccatcccacc cagctggcag     720
gaggttccaa gggcctaggg cttgagactc tggacaactg tagaaaggca catgcagagc     780
tgtcacagga ggtacaaaga ctgacgagtc tgctgcaaca gcatggaatc ccccacactc     840
agcccacaga aaccactcac tctcagcacc tgggtcagca gctccccata ggtgcaatcg     900
cagcagagca tctgcggagt gacccaggac tacgtgggaa catcctgtga gcaaggtggc     960
cacgaagaat agaaatatcc tgagctttga gtgtcctttc acagagtgaa caaaactggt    1020
gtggtgtaga cacggcttct tttggcatat tctagatcag acagtgtcac tgacaaacaa    1080
gagggacctg ctggccagcc tttgttgtgc ccaaagatcc agacaaaata aagattcaaa    1140
gttttaatta attccatact gataaaaaat aactccatga cttctgtaaa ccattgcata    1200
aatgctattg taaaaaaaat taaacaaatg ttaacaactt taacaattca ctaaagtaaa    1260
tggttatgta ttataaatat gaccatctgg gttaagaaga ttccattcac ataacattct    1320
caactaattt ctgaagaaca aatgaacaca aaggcttcca taagttaatc cacatgcgca    1380
tccatactgg gggaaggcct gccaaccagg tacacaagac tctgacacta ccatatactg    1440
ttactattca acactagaga gttagacgac aacaggcatc aggacagtgg tgggtcccag    1500
ttcctagacc catggcccca cctccattac ccacacacgg gccttaaggc tctctctccc    1560
cttcttggcc cttcccaccc agggtagatc ctagaagcct cagctcctaa gaggtctgga    1620
atggatggga aaagtggccc cttctgggac gttctttggt cctcccctgc acacctgtcc    1680
tcagagctca gcctgattcc agaagagcag atgctcagga aagctccccg catgggatgg    1740
gacccagggt gcactaccgc ctgcctcccc agccatcaca acagcccag aactgcccag    1800
ccccagcctg gaatgtcagc ccaggaggag ttaaccagag tagcttacat acaatctaaa    1860
gcttaatgta actgtataca acttgaaatt gtcccgatga gctatcaatc acaaacactg    1920
tcctgttacc acagagacca aaagcctgac atgggaaaca gttcataaat atgaataaaa    1980
ataaacaatc ttaaaccatg gtaacagtag caccaaatac acatgatcta ggtactgagc    2040
taataaatca ttatcactat aattaaaaac aaaagtcact gaaatcaggt caatagttac    2100
cttattaagt agtgggctag ctgtggaatg ttgaagatcc atttccttta aaatgatata    2160
ggtcttttct atcagtttgt cttatattaa aaaatgcttt taaatttcct actatattaa    2220
```

```
atacattcta atttggtcac tgata                                          2245
```

<210> SEQ ID NO 18
<211> LENGTH: 171
<212> TYPE: DNA
<213> ORGANISM: Homo sapiens

<400> SEQUENCE: 18

```
actagtcacc aaaatgcttg gttctaagtg gtagagaagg agacacctta gatataatac     60
aggtcaactt tttgacgtgg ggtgggggtg ggggtggggg tggggggtgaa catcacggtc    120 gcaaataagc agggtttgag ctttgtccag attgtagact taataaaatt y             171
```

<210> SEQ ID NO 19
<211> LENGTH: 491
<212> TYPE: DNA
<213> ORGANISM: Homo sapiens

<400> SEQUENCE: 19

```
cagttgcaga agggagaaat cacggcagaa tcatcgagaa acctgaaaaa tgagacctag     60
aatgaagtat tccaactcca agatttcccc ggcaaagttc agcagcaccg caggcgaagc    120
cctggtcccg ccttgcaaaa taagaagatc ccaacataag accaaagaat tctgccatgt    180
ctactgcatg agactccgtt ctggcctcac cataagaaag gagactagtt attttaggaa    240
agaacccacg aaaagatatt cactaaaatc gggtaccaag catgaagaga acttctctgc    300
ctatccacgg gattctagga agagatcctt gcttggcagt atccaagcat ttgctgcgtc    360
tgttgacaca ttgagcatcc aaggaacttc acttttaaca cagtctcctg cctccctgag    420
tacatacaat gaccaatctg ttagttttgt tttggagaat ggatgttatg tgatcaatgt    480
tgacgactct g                                                         491
```

<210> SEQ ID NO 20
<211> LENGTH: 659
<212> TYPE: DNA
<213> ORGANISM: Homo sapiens

<400> SEQUENCE: 20

```
atttggaatt ttaagtttta tcaatgcttc tggaagctta gaactgtaca cgtgtgatgt     60
cagtcacata gaggaatgtg cccggactgc ctcatgcctt tattttcctt ggtaaatttg    120
aagatagaat gtctgactag cgcagtgacc agaaaacaat gtggtagtca acatctcagg    180
ccatatttta agatcctgta gagcactatt catttcaggt tgcagatgga gtattttga    240 aacatcatta ctatgtagat gcttggatag gagtgagggg gagctagcag atttcctgtg    300
ccatttattc agctgattga tgtacagatg taggtttatt ttgtaaaatc cactgaaaga    360
atatggccac acccttgcct acttgatagc atcaatacag aagccaagaa ggaccactaa    420
gtaaccccct cttcccaggg agagcagcta gcttgaaatc tctcggatac aatcgatgcg    480
tctgaccttt gggatcctca ccatatgggc aaacaatggg ctttgcagga tgagagacac    540
ccacttaaac ctctgacgat ctcgaatggt tcatctcttc cgtcattaac cagtcatgga    600
aaacaatcaa caaactctgc cacgtgaaat attttttcag actttctaa cccaagctt     659
```

<210> SEQ ID NO 21
<211> LENGTH: 341
<212> TYPE: DNA
<213> ORGANISM: Homo sapiens

<400> SEQUENCE: 21

```
raattcaaac aaagctttgg acaaggcccg gttaaaaagc aaagatgtca agttggcaga      60
gactcatcag caggaatgct gccagaagtt tgaacagctt tctgaatctg caaagaaga     120
gctgataaac ttcaaacgga agagagtggc agcatttcga agaacctaa tcgaaatgtc     180
tgaactggaa ataaagcatg ccagaaacaa cgtctccctg ttgcagagct gcatcgactt    240
attcaagaac aactgacctg tctactctga aggacaccaa tgtgaaagcc agcatcactt    300
gcacttaaat cattactgca aaagaaatag ctttgactag t                        341
```

<210> SEQ ID NO 22
<211> LENGTH: 53
<212> TYPE: DNA
<213> ORGANISM: Homo sapiens

<400> SEQUENCE: 22

```
ggatcctgca aggctttggc cagctcagaa gcggcaaccc ctacacacct agg            53
```

<210> SEQ ID NO 23
<211> LENGTH: 21
<212> TYPE: DNA
<213> ORGANISM: Artificial Sequence
<220> FEATURE:
<223> OTHER INFORMATION: chemically synthesized PCR primer

<400> SEQUENCE: 23

```
tcaatggaac cttcagcctt a                                              21
```

<210> SEQ ID NO 24
<211> LENGTH: 25
<212> TYPE: DNA
<213> ORGANISM: Artificial Sequence
<220> FEATURE:
<223> OTHER INFORMATION: chemically synthesized PCR primer

<400> SEQUENCE: 24

```
ctcactgtga aagctgcagc accag                                          25
```

<210> SEQ ID NO 25
<211> LENGTH: 19
<212> TYPE: DNA
<213> ORGANISM: Artificial Sequence
<220> FEATURE:
<223> OTHER INFORMATION: chemically synthesized PCR primer

<400> SEQUENCE: 25

```
gaagggtgg gttttgaag                                                  19
```

<210> SEQ ID NO 26
<211> LENGTH: 2305
<212> TYPE: DNA
<213> ORGANISM: Mus musculus

<400> SEQUENCE: 26

```
atcgcaggag gccgacactg tgactcctgg tggatcggga ctggggagtc agagtcaagc     60
cctgactggt tgcaggcgct cggagtcagc atggaaagtc tctgcggggt cctgggattt    120
ctgctgctgg ctgcaggact gcctctccag gctgccaagc gatttcgtga tgtgctgggc    180
catgaacagt atcccgatca catgagagag cacaaccaat tacgtggctg gtcttcggat    240
gaaaatgaat gggatgaaca cctgtatcca gtgtggagga gggagacgg caggtggaag    300
gactcctggg aaggaggccg tgtgcaggca gtcctgacca gtgactcacc ggctctggtg    360
```

```
ggttccaata tcactttgt ggtgaacctg gtgttccca gatgccagaa ggaagatgct      420
aatggcaata tcgtctatga aagaactgc aggaatgatt tgggactgac atctgacctg      480
catgtctaca actggactgc aggggcagat gatggtgact gggaagatgg caccagccga      540
agccagcatc tcaggttccc ggacaggagg cccttccctc cccccatgg atggaagaaa      600 tggagctttg tctacgtctt tcacacactt ggccagtatt tccaaaaact gggtcggtgt      660
tcagcacggg tttctataaa cacagtcaac ttgacagctg ccctcaggt catggaagtg      720 actgtctttc gaagatacgg ccgggcatac attcccatct cgaaggtgaa agatgtgtat      780
gtgataacag atcagatccc tgtattcgtg accatgtccc agaagaatga caggaacttg      840
tctgatgaga tcttcctcag agacctcccc atcgtcttcg atgtcctcat tcatgatccc      900
agccacttcc tcaacgactc tgccatttcc tacaagtgga actttgggga caacactggc      960
ctgtttgtct ccaacaatca cactttgaat cacacttatg tgctcaatgg aaccttcaac      1020
cttaacctca ccgtgcaaac tgcagtgccc gggccatgcc ctcccccttc gccttcgact      1080
ccgccttcac cttcaactcc gcccttacct tcgccctcac ctttgcccac attatcaaca      1140
cctagcccct ctttaatgcc tactggttac aaatccatgg agctgagtga catttccaat      1200
gaaaactgcc gaataaacag atatggctac ttcagagcca ccatcacaat tgtagagggg      1260
atcctggaag tcagcatcat gcagatagca gatgtcccca tgcccacacc gcagcctgcc      1320
aactccctga tggacttcac tgtgacctgc aaaggggcca cccccatgga agcctgtacg      1380
atcatctccg accccacctg ccagatcgcc cagaaccggg tctgcagccc tgtggctgtg      1440
gatgggctgt gcctgctgtc tgtgagaaga gccttcaatg ggtctggcac ctactgtgtg      1500
aatttcactc tgggagatga tgcaagcctg ccctcacca gcaccctgat ctctatccct      1560
ggcaaagacc cagactcccc tctgagagca gtgaatggtg tcctgatctc catcggctgc      1620
ctggctgtgc ttgtcaccat ggttaccatc ttgctgtaca aaaacacaa ggcgtacaag      1680 ccaataggaa actgccccag gaacacggtc aagggcaagg gcctgagtgt tctcctcagt      1740
cacgcgaaag ccccgttctt ccgaggagac caggagaagg atccattgct ccaggacaag      1800
ccaaggacac tctaagtctt tggccttccc tctgaccagg aacccactct tctgtgcatg      1860
tatgtgagct gtgcagaagt atgtggctgg gaactgttgt tctctaagga ttattgtaaa      1920
atgtatatcg tggcttaggg agtgtggtta aatagcattt tagagaagac atgggaagac      1980
ttagtgtttc ttcccatctg tattgtggtt tttacactgt tcgtggggtg gacacgctgt      2040
gtctgaaggg gaggtggggt cactgctact taaggtccta ggttaactgg gggagatacc      2100
acagatgcct tcagctttcc acataacatg ggcatgaacc cagctaatca ccacctgaag      2160
gccatgcttc atctgccttc caactcactg agcatgcctg agctcctgac aaaattataa      2220
tgggcccggg cttttgtgta tgggtgccgt gtggtgtaca tattctactc attaaaaaag      2280
gcagtctaaa aaaaaaaaaa aaaaa                                            2305
```

<210> SEQ ID NO 27  
<211> LENGTH: 573  
<212> TYPE: PRT  
<213> ORGANISM: Mus musculus

<400> SEQUENCE: 27

Met Glu Ser Leu Cys Gly Val Leu Gly Phe Leu Leu Leu Ala Ala Gly  
1               5                   10                  15

```
Leu Pro Leu Gln Ala Ala Lys Arg Phe Arg Asp Val Leu Gly His Glu
            20                  25                  30

Gln Tyr Pro Asp His Met Arg Glu His Asn Gln Leu Arg Gly Trp Ser
        35                  40                  45

Ser Asp Glu Asn Glu Trp Asp Glu His Leu Tyr Pro Val Trp Arg Arg
 50                  55                  60

Gly Asp Gly Arg Trp Lys Asp Ser Trp Glu Gly Arg Val Gln Ala
 65                  70                  75                  80

Val Leu Thr Ser Asp Ser Pro Ala Leu Val Gly Ser Asn Ile Thr Phe
                85                  90                  95

Val Val Asn Leu Val Phe Arg Cys Gln Lys Glu Asp Ala Asn Gly Asn
            100                 105                 110

Ile Val Tyr Glu Lys Asn Cys Arg Asn Asp Leu Gly Leu Thr Ser Asp
            115                 120                 125

Leu His Val Tyr Asn Trp Thr Ala Gly Ala Asp Asp Gly Asp Trp Glu
    130                 135                 140

Asp Gly Thr Ser Arg Ser Gln His Leu Arg Phe Pro Asp Arg Arg Pro
145                 150                 155                 160

Phe Pro Arg Pro His Gly Trp Lys Lys Trp Ser Phe Val Tyr Val Phe
                165                 170                 175

His Thr Leu Gly Gln Tyr Phe Gln Lys Leu Gly Arg Cys Ser Ala Arg
            180                 185                 190

Val Ser Ile Asn Thr Val Asn Leu Thr Ala Gly Pro Gln Val Met Glu
            195                 200                 205

Val Thr Val Phe Arg Arg Tyr Gly Arg Ala Tyr Ile Pro Ile Ser Lys
    210                 215                 220

Val Lys Asp Val Tyr Val Ile Thr Asp Gln Ile Pro Val Phe Val Thr
225                 230                 235                 240

Met Ser Gln Lys Asn Asp Arg Asn Leu Ser Asp Glu Ile Phe Leu Arg
                245                 250                 255

Asp Leu Pro Ile Val Phe Asp Val Leu Ile His Asp Pro Ser His Phe
            260                 265                 270

Leu Asn Asp Ser Ala Ile Ser Tyr Lys Trp Asn Phe Gly Asp Asn Thr
            275                 280                 285

Gly Leu Phe Val Ser Asn Asn His Thr Leu Asn His Thr Tyr Val Leu
    290                 295                 300

Asn Gly Thr Phe Asn Leu Asn Leu Thr Val Gln Thr Ala Val Pro Gly
305                 310                 315                 320

Pro Cys Pro Pro Ser Pro Ser Thr Pro Pro Ser Pro Ser Thr Pro
                325                 330                 335

Pro Leu Pro Ser Pro Ser Pro Leu Pro Thr Leu Ser Thr Pro Ser Pro
            340                 345                 350

Ser Leu Met Pro Thr Gly Tyr Lys Ser Met Glu Leu Ser Asp Ile Ser
            355                 360                 365

Asn Glu Asn Cys Arg Ile Asn Arg Tyr Gly Tyr Phe Arg Ala Thr Ile
370                 375                 380

Thr Ile Val Glu Gly Ile Leu Glu Val Ser Ile Met Gln Ile Ala Asp
385                 390                 395                 400

Val Pro Met Pro Thr Pro Gln Pro Ala Asn Ser Leu Met Asp Phe Thr
                405                 410                 415

Val Thr Cys Lys Gly Ala Thr Pro Met Glu Ala Cys Thr Ile Ile Ser
            420                 425                 430

Asp Pro Thr Cys Gln Ile Ala Gln Asn Arg Val Cys Ser Pro Val Ala
```

-continued

```
                435                 440                 445
Val Asp Gly Leu Cys Leu Leu Ser Val Arg Arg Ala Phe Asn Gly Ser
    450                 455                 460

Gly Thr Tyr Cys Val Asn Phe Thr Leu Gly Asp Asp Ala Ser Leu Ala
465                 470                 475                 480

Leu Thr Ser Thr Leu Ile Ser Ile Pro Gly Lys Asp Pro Asp Ser Pro
                485                 490                 495

Leu Arg Ala Val Asn Gly Val Leu Ile Ser Ile Gly Cys Leu Ala Val
            500                 505                 510

Leu Val Thr Met Val Thr Ile Leu Leu Tyr Lys Lys His Lys Ala Tyr
        515                 520                 525

Lys Pro Ile Gly Asn Cys Pro Arg Asn Thr Val Lys Gly Lys Gly Leu
    530                 535                 540

Ser Val Leu Leu Ser His Ala Lys Ala Pro Phe Phe Arg Gly Asp Gln
545                 550                 555                 560

Glu Lys Asp Pro Leu Leu Gln Asp Lys Pro Arg Thr Leu
                565                 570
```

METHOD OF DETECTING AND TREATING TUBEROUS SCLEROSIS COMPLEX ASSOCIATED DISORDERS

RELATED APPLICATIONS

This application is a continuation of U.S. Ser. No. 12/080,362, filed Apr. 2, 2008, now abandoned, which is a continuation of U.S. Ser. No. 10/991,173, now abandoned, filed Nov. 16, 2004, which is a continuation of U.S. Ser. No. 10/016,253, filed Dec. 10, 2001, now abandoned, which claims priority to U.S. Provisional Patent Application No. 60/254,268, filed Dec. 8, 2000, each of which is incorporated herein by reference in its entirety.

FIELD OF THE INVENTION

The invention relates to methods of detecting and treating Tuberous Sclerosis Complex (TSC) associated disorders.

INCORPORATION-BY-REFERENCE

SEQUENCE LISTING

The instant application contains a sequence listing which has been submitted via EFS-Web and is hereby incorporated by reference in its entirety. Said ASCII copy, created on Sep. 29, 2014, is named 21402-042C02_SeqList_ST25 and is 35,081bytes in size.

BACKGROUND OF THE INVENTION

The phakomatoses, or 'neuro-cutaneous disorders', are a group of three Mendelian autosomal dominantly inherited diseases that present with phenotypes affecting multiple organ systems in affected individuals. Neuro-cutaneous disorders include for example, Neurofibromatosis (NF), Tuberous Sclerosis (TSC) and Von Hippel-Lindau (VHL). These diseases all produce both neurological and dermatological symptoms.

Tuberous sclerosis complex (TSC) is an autosomal dominant tumor-suppressor gene syndrome, characterized by development of distinctive benign tumors (hamartomas) and malformations (hamartias) in multiple organ systems. The brain, skin, heart, and kidneys are commonly affected. TSC lesions occurring in the skin and kidney contain smooth muscle cells, endothelial cells, adipocytes, and large neuronal appearing cells. Despite this complex cellular architecture, kidney and other lesions in TSC appear to be clonal in nature, based on clonality and loss of heterozygosity (LOH) analyses. In the brain, TSC produces both subependymal tubers that line the ventricular sacs and subcortical hamartomas which serve as foci for epileptic discharges. TSC produces cardiac rhabdomyomas in the fetus/newborn that spontaneously regress in the first year of life. TSC is also associated with renal angiomyolipomas, pulmonary symptoms, and manifestations in other organ systems. In addition, TSC is also associated with multiple dermatological features such as hypomelanotic macules, facial angiofibroma, shagreen patches, and ungual fibromas.

A better understanding of the molecular nature of this disease will provide new therapeutic tools to treat the pathologies associated with TSC complex not only in TSC patients but also in non TSC patients afflicted by similar pathologies.

SUMMARY OF THE INVENTION

The present invention is based in part on the discovery of changes in expression patterns of multiple nucleic acid sequences in cells derived from the Tsc2 knockout transgenic mice compared to the expression pattern found in cells derived from Tsc2+/− heterozygote and wild type sibling mice. These differentially expressed nucleic acids include previously undescribed sequences and nucleic acids sequences that, while previously described, have not heretofore been identified as TSC modulated.

In various aspects, the invention includes methods of diagnosing or determining susceptibility to Tuberous Sclerosis Complex (TSC) associated disorder, and methods of treating those disorders. For example, in one aspect, the invention provides a method of diagnosing determining susceptibility to a tuberous sclerosis complex associated disorder by providing a test cell population that includes one or more cells capable of expressing one or more TSC modulated nucleic acids sequences. Levels of expression of one or more sequences, termed TSCX sequences, are then compared to the levels of expression of the corresponding nucleic acids in a reference cell population. The reference cell population contains cells whose tuberous sclerosis complex associated disorder status is known, i.e., the reference cells are known to have or are known not to have a tuberous sclerosis associated disorder.

The invention in another aspect includes a method of identifying a therapeutic agent for treating a tuberous sclerosis complex associated disorder. The method includes providing from the subject a test cell population comprising a cell capable of expressing one or more TSCX nucleic acids sequences, contacting the test cell population with the therapeutic agent, and comparing the expression of the nucleic acids sequences in the test cell population to the expression of the nucleic acids sequences in a reference cell population.

The invention in a further aspect includes a method of selecting an individualized therapeutic agent appropriate for a particular subject. The method includes providing from the subject a test cell population comprising a cell capable of expressing one or more TSCX nucleic acids sequences, contacting the test cell population with the therapeutic agent, and comparing the expression of the nucleic acids sequences in the test cell population to the expression of the nucleic acids sequences in a reference cell population.

Also provided are novel nucleic acids, as well as their encoded polypeptides, which are tuberous sclerosis complex modulated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

The present invention is based in part on the discovery of changes in expression patterns of multiple nucleic acid sequences in cells derived from the Tsc2 knockout transgenic mice compared to the expression pattern found in cells derived from Tsc2+/− heterozygote and wild type sibling mice.

The change is expression pattern was identified by GeneCalling™ analysis (U.S. Pat. No. 5,871,697; Shimkets et al., 1999 Nature Biotechnology 17:198-803, incorporated herein by reference in their entireties) of neuronal stem cell (NSC) and mouse emroyonic fibroblasts (MEF) cell lines established from 10-11 day embryos from mice of the three genotypes (i.e.)

A summary of the sequences analyzed are presented in Table 1. The 142 single nucleic acid sequences identified herein, are referred to herein as TSC 1-142 or TSCX nucleic acids or polypeptides. Differential expression of TSC 1-142 gene fragments was confirmed using a unlabeled oligonucleotide competition assay as described in Shimkets et al., Nature Biotechnology 17:198-803.

By comparing the genes differentially expressed in both cell lines it was possible to identify understand common mechanisms in TSC –/– tumor formation. Whereas, by comparing the genes differentially expressed in NSC cell lines it was identify genes that are expressed in cells that are the originators (i.e., progenitors) of TSC tumors. Based on the TSC phenotype, genes that are up-regulated in the TSC-cells may have a role in cancer progression, specifically for renal and lung carcinomas Twenty-six sequences (TSC: 1-26) represent novel murine genes for which the sequence identity to sequences found in public databases suggesting a putative homology.

The 116 other sequenced identified have been previously described. For some of the novel sequences (i.e., TSC: 1-26), a cloned sequence is provided along with one or more additional sequence fragments (e.g., ESTs or contigs) which contain sequences substantially identical to, the cloned sequence. Also provided is a consensus sequences which includes a composite sequence assembled from the cloned and additional fragments. For a given TSC sequence, its expression can be measured using any of the associated nucleic acid sequences may be used in the methods described herein. For previously described sequences database accession numbers are provided. This information allows for one of ordinary skill in the art to deduce information necessary for detecting and measuring expression of the TSC nucleic acid sequences.

A subset of the TSC modulated genes can be further subdivided into three classes:

A. Secreted and/or Membrane Bound Proteins that are Up-Regulated in Cell Derived from Tsc2 Knockout Transgenic Mice Proteins in this category include, Plasma phospholipid transfer protein, Lysyl hydroxylase isoform 2, DVS27-related protein [AB024518], Cathepsin L, Tenascin, ADAMTS1, Tissue inhibitor of metalloproteinase-2, Integrin beta-5, Thrombospondin 2 (THBS2) Aspartyl protease 1, Cyr61, Tetraspan NET-7, Cysteine-rich glycoprotein SPARC, neuronal pentraxin receptor, ITM2B-E25B protein Integral Membrane Protein 2B, transmembrane glycoprotein NMB, and zinc finger protein These proteins are potential candidates for antibody screening and antibody-binding therapy for the treatment of TSC and TSC related diseases.

B. Secreted and/or Membrane Bound Proteins that are Down-Regulated in Cell Derived from Tsc2 Knockout Transgenic Mice Proteins in this category include, Growth/differentiation factor 1 (GDF-1), Extracellular matrix associated protein (Sc1), Membrane-type 2 matrix metalloproteinase and Thrombospondin 1 mice.

These proteins that are potential candidates for the treatment of TSC and TSC related diseases.

C. Protein with Enzymatic Activities

Proteins in this category include Growth factor-inducible immediate early gene 3CH134/erp, Galactokinase 1, Serum inducible kinase (SNK), PAF acetylhydrolase Aspartyl protease 1, Lysyl hydroxylase isoform 2 Peroxisomal D2, and D4-dienoyl-CoA reductase (Pdcr).

These proteins are potential candidates for small molecule screening and small molecule drug therapy for the treatment of TSC and TSC related diseases.

The TSC modulated nucleic acids discussed herein include the following:

TABLE 1

| Gene Discovered | TSCX Assignment | SEQ ID NO | Acc # | MEF +/– TSC2 vs. +/+ TSC2 (16606) | MEF –/– TSC2 vs. +/+ TSC2 (16607) | NSC +/– TSC2 vs. +/+ TSC2 (16608) | NSC –/– TSC2 vs. +/+ TSC2 (16609) |
|---|---|---|---|---|---|---|---|
| Novel gene fragment, 2520 bp | 1 | 1 | aa914498 | ±1.0 | +1.5 | +2 | +1.5 |
| Novel gene fragment, 1863 bp | 2 | 2 | aa073509 | ±1.0 | –6 | –2 | –2 |
| Novel gene fragment, 750 bp | 3 | 3 | AA183535 | ±1.0 | +3 | ±1.0 | +4 |
| Novel gene fragment, 281 bp, 91% AA identity to rat Steroid sensitivity gene-1 protein [AAF35351] | 4 | 4 | | ±1.0 | –1.5 | ±1.0 | NEW |
| Novel gene fragment, 1568 bp, 86% SI to human Tetraspan NET-7 [AF120266]/old brain study also | 5 | 5 | | ±1.0 | X | +2 | +6 |
| Novel gene fragment, 300 bp, 94% SI to rat 10-formyltetrahydrofolate dehydrogenase [M59861] | 6 | 6 | | O | O | O | +15 |
| Novel gene fragment, 965 bp, 86% SI to rat myr3 myosin I heavy chain [X74815] | 7 | 7 | | –2 | X | ±1.0 | NEW |
| Novel gene fragment, 408 bp, 97% SI to rat Limbic system-associated membrane protein [U31554] | 8 | 8 | | O | O | ±1.0 | OFF |
| Novel gene fragment, 777 bp, 83% SI to rat neuronal pentraxin receptor [AF005099] | 9 | | | ±1.0 | ±1.0 | ±1.0 | NEW |
| Novel gene fragment, 354 bp, 87% SI to human KIAA0631 [AB014531] | 10 | 9 | | ±1.0 | X | –2 | –5 |
| Novel gene fragment, 955 bp | 11 | 10 | | ±1.0 | X | –3 | –8 |
| Novel gene fragment, 1113 bp | 12 | 11 | | +2 | X | ±1.0 | –9 |
| Novel gene fragment, 918 bp | 13 | | | ±1.0 | ±1.0 | ±1.0 | +3 |
| Novel gene fragment, 1166 bp | 14 | | | ±1.0 | ±1.0 | ±1.0 | +10 |
| Novel gene fragment, 594 bp | 15 | 12 | | ±1.0 | ±1.0 | ±1.0 | –10 |
| Novel gene fragment, 713 bp | 16 | 13 | | O | O | ±1.0 | OFF |

TABLE 1-continued

| Gene Discovered | TSCX Assignment | SEQ ID NO | Acc # | MEF +/− TSC2 vs. +/+ TSC2 (16606) | MEF −/− TSC2 vs. +/+ TSC2 (16607) | NSC +/− TSC2 vs. +/+ TSC2 (16608) | NSC −/− TSC2 vs. +/+ TSC2 (16609) |
|---|---|---|---|---|---|---|---|
| Novel gene fragment, 306 bp, 95% SI to rat ribosomal protein L13a [X68282] | 17 | 14 | | ±1.0 | −2 | ±1.0 | X |
| Novel gene fragment, 66 bp, 96% SI to rat ribosomal protein S20 [X51537] | 18 | 15 | | ±1.0 | −2 | −2 | ±1.0 |
| Novel gene fragment, 1613 bp | 19 | 16 | | ±1.0 | +3 | ±1.0 | −5 |
| Novel gene fragment, 2245 bp | 20 | 17 | | ±1.0 | NEW | −2 | −3 |
| Novel gene fragment, 171 bp, 86% SI to rat nonmuscle caldesmon [U18419] | 21 | 18 | | | ±1.0 | | +1.5 |
| Novel gene fragment, 491 bp, 72% SI to human DVS27-related protein [AB024518] | 22 | 19 | | | | | +10 |
| Novel gene fragment, 659 bp, 72% SI to human ATP cassette binding transporter 1 [AF165281] | 23 | 20 | | −2 | X | ±1.0 | NEW |
| Novel gene fragment, 341 bp, 84% SI to human sorting nexin 5 (SNX5) [AF121855] | 24 | 21 | | | | | |
| Novel gene fragment, 53 bp, 84% SI to rat calcium-independent alpha-latrotoxin receptor [U72487] | 25 | 22 | | | | | |
| Novel gene fragment, 52 bp, 98% SI to rat Na+,K+-ATPase alpha(+) isoform catalytic subunit [M14512] | 26 | | | | −2 | | |
| MEF & NSC −/− conserved differential expression | | | | | | | |
| Ribosomal protein L8 (RPL8) | 27 | | U67771 | −9 | OFF | −3 | OFF |
| Alpha-B crystallin (p23) | 28 | | M63170 | ±1.0 | +20 | +2 | +7 |
| Tumor cell dnaJ-like protein 1 | 29 | | L16953 | ±1.0 | +2 | +3 | +2 |
| Insulin-like growth factor-binding protein-4 | 30 | | S80566 | ±1.0 | −2 | +3 | OFF |
| Insulin-like growth factor binding protein 5 (IGFBP5) | 31 | | L12447 | ±1.0 | NEW | +2 | +5 |
| Rac1 | 32 | | X57277 | −2 | −1.5 | −2 | −2 |
| Growth factor-inducible immediate early gene 3CH134/erp | 33 | | S64851 | ±1.0 | +2 | ±1.0 | +6 |
| Phosphatidic acid phosphatase type 2c (Ppap2c) | 34 | | AF123611 | ±1.0 | −5 | ±1.0 | −4 |
| Annexin III | 35 | | AJ001633 | ±1.0 | NEW | ±1.0 | NEW |
| Taipoxin-associated calcium binding protein 49 | 36 | | AF049125 | ±1.0 | −2 | ±1.0 | OFF |
| C-fos oncogene | 37 | | V00727 | +2 | +1.5 | ±1.0 | NEW |
| Stra13 | 38 | | AF010305 | +2 | +6 | ±1.0 | +2 |
| E1B 19K/Bcl-2-binding protein homolog (Nip3) | 39 | | AF041054 | +2 | +5 | ±1.0 | +3 |
| Peroxisomal D2,D4-dienoyl-CoA reductase (Pdcr) | 40 | | AF155575 | +7 | NEW | +2 | NEW |
| Galactokinase 1 | 41 | | AB027012 | ±1.0 | +4 | ±1.0 | +1.5 |
| Alpha-enolase (2-phospho-D-glycerate hydrolase) (NNE) | 42 | | X52379 | +3 | +5 | +3 | +15 |
| Alpha-N-acetylglucosaminidase | 43 | | AF003255 | ±1.0 | +2 | ±1.0 | +3 |
| Uncoupling protein 2 (UCP2) | 44 | | AF111998 | ±1.0 | NEW | +2 | NEW |
| ANC1 for adenine nucleotide carrier | 45 | | X74510 | ±1.0 | −1.5 | ±1.0 | −2 |
| Vacuolar ATPase subunit A gene | 46 | | U13837 | ±1.0 | +3 | ±1.0 | +2 |
| S-adenosylmethionine decarboxylase | 47 | | D12780 | ±1.0 | +2 | ±1.0 | +5 |
| Spermidine/spermine N1-acetyltransferase (SSAT) | 48 | | L10244 | ±1.0 | +5 | ±1.0 | +4 |
| Xanthine dehydrogenase | 49 | | X62932 | ±1.0 | +9 | ±1.0 | NEW |
| MBOCT | 50 | | AB012808 | ±1.0 | OFF | ±1.0 | −3 |
| Plasma phospholipid transfer protein | 51 | | U37226 | ±1.0 | +2 | −2 | +5 |
| Lysyl hydroxylase isoform 2 | 52 | | AF080572 | +3 | +6 | ±1.0 | NEW |
| Cathepsin L | 53 | | J02583 | ±1.0 | +5 | ±1.0 | +4 |
| Ezrin | 54 | | X60671 | +2 | +4 | ±1.0 | +4 |
| Thy-1.2 glycoprotein | 55 | | M12379 | −2 | −4 | ±1.0 | −10 |
| A-X actin | 56 | | J04181 | +5 | NEW | +6 | NEW |
| MHC class I heavy chain precursor (H-2D(b)) | 57 | | U47325 | +3 | +2 | ±1.0 | +4 |
| MHC class I heavy chain precursor (H-2K(b)) | 58 | | U47328 | +2 | NEW | ±1.0 | +3 |
| MHC region containing the Q region of class I | 59 | | AF111103 | ±1.0 | +4 | −2 | NEW |
| NGF-inducible protein TIS21 (aka BTG2) | 60 | | M64292 | +2 | +2 | ±1.0 | NEW |
| Ndr1 | 61 | | U60593 | +2 | +8 | ±1.0 | NEW |
| Gly96 | 62 | | X67644 | +2 | +3 | ±1.0 | +2 |
| p8 protein | 63 | | AF131196 | +2 | +4 | ±1.0 | +5 |
| MEF & NSC −/− opposite differential expression | | | | | | | |
| Adrenomedullin precursor | 64 | | U77630 | ±1.0 | OFF | ±1.0 | NEW |
| Fibroblast growth factor | 65 | | M65053 | ±1.0 | −3 | −2 | +2 |
| Serum inducible kinase (SNK) | 66 | | M96163 | ±1.0 | −3 | +2 | NEW |
| Annexin VI | 67 | | X13460 | ±1.0 | −2 | ±1.0 | NEW |

TABLE 1-continued

| Gene Discovered | TSCX Assignment | SEQ ID NO | Acc # | MEF +/− TSC2 vs. +/+ TSC2 (16606) | MEF −/− TSC2 vs. +/+ TSC2 (16607) | NSC +/− TSC2 vs. +/+ TSC2 (16608) | NSC −/− TSC2 vs. +/+ TSC2 (16609) |
|---|---|---|---|---|---|---|---|
| Annexin I | 68 | | X07486 | −2 | −1.5 | +2 | +10 |
| Annexin II | 69 | | D10024 | ±1.0 | −4 | +2 | +2 |
| AP-2 transcription factor | 70 | | X57012 | ±1.0 | OFF | ±1.0 | +20 |
| Jun-B | 71 | | J03236 | +2 | −4 | ±1.0 | NEW |
| PAF acetylhydrolase | 72 | | U34277 | ±1.0 | OFF | ±1.0 | +12 |
| Phosphomannomutase | 73 | | AF007267 | ±1.0 | +3 | −2 | −3 |
| Sodium/potassium ATPase beta subunit | 74 | | X61433 | +3 | +8 | −2 | −12 |
| Thioredoxin | 75 | | X77585 | ±1.0 | +1.5 | +2 | −3 |
| Spermidine synthase | 76 | | L19311 | ±1.0 | +2 | ±1.0 | −2 |
| Aldehyde dehydrogenase II | 77 | | M74570 | +2 | NEW | ±1.0 | OFF |
| Voltage dependent anion channel 2 | 78 | | U30838 | +2 | +2 | ±1.0 | −2 |
| Tenascin | 79 | | D90343 | ±1.0 | −5 | +2 | +4 |
| ADAMTS1 | 80 | | D67076 | −2 | −2 | ±1.0 | +2 |
| Tissue inhibitor of metalloproteinase-2 | 81 | | M93954 | ±1.0 | −2 | ±1.0 | +3 |
| Integrin beta-5 | 82 | | AF022110 | ±1.0 | −3 | ±1.0 | +1.5 |
| Thrombospondin 2 (THBS2) | 83 | | L07803 | ±1.0 | −6 | ±1.0 | NEW |
| Membrane glycoprotein M6 = major CNS myelin protein PLP/DM20 homolog | 84 | | S65735 | +2 | NEW | ±1.0 | −4 |
| Gelsolin | 85 | | J04953 | ±1.0 | −2 | ±1.0 | NEW |
| Gag = antigen LEC-A, env | 86 | | S74315 | ±1.0 | −2 | ±1.0 | +5 |
| NSC only | 87 | | | | | | |
| Quaking type I (QKI) | 88 | | U44940 | ±1.0 | ±1.0 | ±1.0 | −1.5 |
| mSin3B | 89 | | L38622 | ±1.0 | ±1.0 | ±1.0 | +2 |
| Retinoblastoma susceptibility protein (pp105 Rb) | 90 | | M26391 | ±1.0 | ±1.0 | ±1.0 | +1.5 |
| Heat shock protein (hsp-E7I) | 91 | | L40406 | ±1.0 | ±1.0 | ±1.0 | +2 |
| Aspartyl protease 1 | 92 | | AF216310 | ±1.0 | ±1.0 | ±1.0 | +10 |
| Placental growth factor-1 (p1GF) | 93 | | X80171 | ±1.0 | ±1.0 | ±1.0 | +3 |
| Growth/differentiation factor 1 (GDF-1) | 94 | | M62301 | ±1.0 | X | ±1.0 | OFF |
| Calgizzarin/S100A11 | 95 | | U41341 | ±1.0 | ±1.0 | +2 | +15 |
| Cyr61 | 96 | | M32490 | +2 | ±1.0 | ±1.0 | +25 |
| ADP-ribosylation factor-directed GTPase activating protein isoform b (Shag1) | 97 | | AF075462 | ±1.0 | X | −2 | −2 |
| Camk-2 mRNA for Ca2+/calmodulin dependent protein kinase | 98 | | X63615 | ±1.0 | ±1.0 | ±1.0 | −10 |
| MAPKAPK5 mitogen-activated protein kinase-activated protein kinase | 99 | | AF039840 | −2 | ±1.0 | −2 | −2 |
| Fyn proto-oncogene encoding p59fyn | 100 | | M27266 | ±1.0 | ±1.0 | ±1.0 | −2 |
| Beta 1,4N-acetylgalactosaminyltransferase | 101 | | L25885 | ±1.0 | X | ±1.0 | +1.5 |
| Muscle glycogen phosphorylase (Pygm) | 102 | | AF124787 | ±1.0 | X | +2 | OFF |
| Protein phosphatase 1 binding protein PTG | 103 | | U89924 | ±1.0 | X | ±1.0 | −4 |
| Argininosuccinate synthetase (Ass) | 104 | | M31690 | +2 | X | ±1.0 | NEW |
| Phospholipid hydroperoxide glutathione peroxidase (Gpx4) | 105 | | AF045769 | ±1.0 | ±1.0 | ±1.0 | +5 |
| GABA transporter (GAT4) | 106 | | L04662 | ±1.0 | ±1.0 | −2 | OFF |
| Sodium bicarbonate cotransporter NBC1 | 107 | | AF141934 | −3 | X | −3 | −2 |
| Glial fibrillary acidic protein (GFAP) | 108 | | K01347 | O | O | O | NEW |
| Tropomodulin | 109 | | S76831 | ±1.0 | X | ±1.0 | NEW |
| Cysteine-rich glycoprotein SPARC | 110 | | X04017 | ±1.0 | ±1.0 | −2 | +10 |
| DSD-1-proteoglycan | 111 | | AJ133130 | ±1.0 | ±1.0 | ±1.0 | OFF |
| Extracellular matrix associated protein (Sc1) | 112 | | U64827 | ±1.0 | X | ±1.0 | −1.5 |
| Membrane-type 2 matrix metalloproteinase | 113 | | D86332 | O | O | −2 | −8 |
| Astrotactin | 114 | | U48797 | O | O | −2 | −10 |
| Adipose differentiation related protein (ADRP) | 115 | | M93275 | ±1.0 | X | +2 | NEW |
| Ventral neuron-specific protein 1 NOVA1 | 116 | | AF232828 | O | ±1.0 | ±1.0 | OFF |
| Neuronal pentraxin 1 (NPTX1) | 117 | | U62021 | −2 | X | ±1.0 | −10 |
| Receptor activity modifying protein 1 (Ramp1) | 118 | | AF209904 | ±1.0 | ±1.0 | +2 | −7 |
| Lunatic fringe | 119 | | AF015768 | ±1.0 | X | ±1.0 | −4 |
| TPA-induced TIS11 | 120 | | X14678 | +2 | ±1.0 | ±1.0 | +6 |
| ITM2B - E25B protein Integral Membrane Protein 2B | 121 | | U76253 | O | O | +6 | NEW |
| NMB | 122 | | aj251685 | −4 | X | ±1.0 | NEW |
| B-cell translocation gene-1 protein (BTG1) | 123 | | L16846 | ±1.0 | ±1.0 | ±1.0 | +2 |
| MEF only | | | | | | | |
| Keratinocyte growth factor/fibroblast growth factor-7 | 124 | | U58503 | ±1.0 | −10 | +3 | X |
| NOV protein | 125 | | Y09257 | +2 | OFF | ±1.0 | X |
| TGF-beta binding protein-2 | 126 | | AF004874 | ±1.0 | −4 | +2 | X |
| GATA-6 = zinc finger transcription factor | 127 | | S82462 | ±1.0 | +4 | ±1.0 | X |
| PDGF-alpha-receptor (PDGF-alpha-R) | 128 | | M84607 | −2 | −6 | ±1.0 | X |
| Vascular smooth muscle alpha-actin | 129 | | X13297 | ±1.0 | −6 | ±1.0 | ±1.0 |
| Alpha-2 collagen VI | 130 | | X65582 | ±1.0 | −8 | ±1.0 | X |
| Laminin alpha 4 chain | 131 | | U69176 | ±1.0 | −4 | O | O |

TABLE 1-continued

| Gene Discovered | TSCX Assignment | SEQ ID NO | Acc # | MEF +/− TSC2 vs. +/+ TSC2 (16606) | MEF −/− TSC2 vs. +/+ TSC2 (16607) | NSC +/− TSC2 vs. +/+ TSC2 (16608) | NSC −/− TSC2 vs. +/+ TSC2 (16609) |
|---|---|---|---|---|---|---|---|
| PGI (biglycan) | 132 | | X53928 | ±1.0 | −5 | +2 | X |
| Thrombospondin 1 | 133 | | M87276 | −2 | −4 | +2 | X |
| Fragile X mental retardation syndrome protein (Fmr1) | 134 | | L23971 | ±1.0 | +3 | ±1.0 | X |
| Osf-2 for osteoblast specific factor 2 | 135 | | D13664 | ±1.0 | −20 | ±1.0 | X |
| Ndr2 | 136 | | AB033921 | ±1.0 | +10 | +2 | ±1.0 |
| P53 | 137 | | X00741 | | | | ±1.0 |
| Tuberin (Tsc2) | 138 | | U37775 | ±1.0 | X | −2 | OFF |
| Alpha glucosidase II alpha subunit | 139 | | U92793 | ±1.0 | ±1.0 | ±1.0 | + |
| DAN | 140 | | D50263 | ±1.0 | Q | ±1.0 | +3 |
| intracisternal A-particle element | 141 | | D49812 | ±1.0 | ±1.0 | +2 | +5 |
| Annexin V | 142 | | U29396 | | | — | +1.5 |

Key =
New = de novo expression
Bold = gene was confirmed in that job
+1.0 = no difference
X = no poison
Q = in process
p = partial poison
O = no band Below follows additional discussion of nucleic acid sequences whose expression is differentially regulated.

TSC1

TSC1 is a novel 2520 bp gene fragment. The nucleic acid was initially identified in a cloned fragment having the following sequence:

```
                                                                       (SEQ ID NO: 1)
  1 GGCTCTGGCTCGGGCTCGGGCTGGGGCTGGGGCTTGGGCTCCAGCTCGGGCCCTGCACCTGTGACTCGGCGGCGTTGCTC    81
    CTCCGCTGCCCCATGGCCCCGTCCCGGCTGCAGCTCGGCCTCCGCGCCGCCTACTCCGGCTTCAGCTCGGTAGCCGGCTT   161
    CTCCATCTTCTTCGTCTGGACGGTGGTCTACCGACAACCGGGGACTGCGGCGATGGGGGTCTCGCAGGTGTCCTGGCAC   241
    TGTGGGTCTTGGTGACTCACGTGATGTACATGCAGGATTACTGGAGGACCTGGCTCAGAGGGCTGCGCGGCTTCTTCTTC   321
    GTGGGTGCTCTCTTCTCGGCAGTCTCCGTTTCCGCCTTCTGCACCTTCCTGGCATTGGCCATCACCCAGCATCAGAGTCT   401
    CAAAGACCCGAACAGCTACTACCTCTCCTGTGTCTGGAGCTTCATTTCCTTCAAGTGGGCCTTCCTACTTAGCCTCTACG   481
    CCCACCGCTACCGGGCTGACTTTGCGGACATCAGCATCCTTAGTGATTTCTAACCCAGGGAATGAGGTCACCACAGCCTG   561
    GGGGCCCTCGGGATCTGGACTCAGCTTCCGAGTCAGCAAGGGAGCTCACCCCAACCCCTGGGGAACTCCAGAACCATGGC   641
    AGAGTATATGGGCCCGTTCAGTTTCTCAGAAATCTGTCTGGTCCCCTTTTGGGGAAGATATAGAGCTGTTAAAGGGATAC   721
    TGCCAATCTGCCCAATCTGCCCGTTAGCCCAGCTAGAGGGCAGCTTAGACCTTTCCAAATAGATCTATTTTCTTAGCCCT   801
    CTGAGGGATCTCTGTAAGTAGGGCCACGACAATGAATTCAATGGGTAGGATTGGAACTATGGCTAGTGACAGGGGCTGGG   881
    ACAGGCTTCCTTGCTACCCCAGACTTCATTGAAGCTGTGTGTGGGGAGGCATCAAAGGTCTGGTCAAGAGAGGAATCTT   961
    TAGTACAGATCTCCATCCCTGTTCCCCACCCTGTTACCCTGAAGTGTCGGGTAGCCAAACTCACCGGTCCTTAGGGAAT  1041
    TGACAATTGGCTCCTTCCCTAAGCAGCACAGTTGGACAGAATCCAGCGTCCGTCCGTCCTACCTTCCCATCCAGAGTTTG  1121
    TTTCCCATGAGGGTGCTAGCGCCAGCCAACCATTCCCATGTGTCGCATATGCACACATGACCACACACACCAGAGCAGGA  1201
    CTCCTCGGATGAGGCTAGACTTGAGGACCACAGGAAACACACCCCTGCACTTAGAAGGGCTTTGGGATCGGGGCAACCT  1281
    GGTGGGGGCAAGTGGGAGCTCTCCATCTGTACTGAGTCTCCAACCTTGCCCCTCACTGCACAAGACCACCCTGACCGTGA  1361
    GGACCTCCTCCCTGCACCAGATCCTAACTCTGACCTTTCACCTTCTCTCTCCTGAAGGAACTCTTCTGAGTGGACATG  1441
    GGCCCAAGGCCTTACCTAAGCGGAGAGGGAGGGCAGGGCTGCTACTCTTCTCTGTAAC CTTCTCTGATGGGTTGTCACT  1521
    TTGCACGTCTACTCTTCCACTTGGGCACTGCCCCAGCTCTCTGCCTTACCTGTGTTATGGGCACTTAAGCAGAAATACA  1601
    GCGGCCATTTTAACCAGCAAAAAAAAAAAAATAGGGGGTGGGCGGTTTTGAGAGGGGACAAGAGTGGGCAAGATGGG   1681
    GGCTCTAGCTGTCTGATCATCTCCCTAAGTTTGGGGCTACTAGACGGTATTCCTCATCTCTGGTCCCCTATGGGAGACCA   1761
    CCAGCTGAGATCTCCTTTGCTCTCCCAGTTCTGTCCCAGCCAGGGTTAGGATGCCCACAGACTCAACATCCCTGCAGATT   1841
```

```
CCATCTCCCCACCCTAAGCCAAGGTAGATGGGAAAGGGAATCTTTCTTTTTCTACCCCAGCCAGACTACTTGGGGCTCCA    1921

AGTTGACCAGGATGTGTGGATTCAGAAGCAGAAAGGCAGGAGCTAGCACCTCTCTCACGCTGGGTACACTTGTCCTGGCC    2001

TGTGTTTGCCTCACCCTGGCCTTTACAGTGTAAAAACACCATGGGACTTTAGAGCAGGGAAGGATAAGGAACAGTGTCAC    2081

TTCTAGAGCCTTCTGCTGGTAGACGCTCCTACTGATAGAGGAGGTAAAGACTACTGACCTCCCGGCTAGGCCTGGCTTAA    2161

GCCAGGCGTGGCCTGCGTCACAACCTTTTGCGGTGTCTTAGCAACCTGAACCTGAGATCTTATTCCCGAATCCCACAGGG    2241

CCCAATGTGCAGGGCTCAGCCTGGGGCCATCTCCCTTTTCACCTGGGTTGGTGAGCATGTATTTGGAGTGGTTTCTTCCT    2321

GCATGTATTAGCCAAGGAAGGACAAGGGACTAGAGGGTCTGAGTTAGGTCCAGACTTGTCCCCTTTCCCCAGCCCATCAC    2401

AGGATGCTGGGTGCACACCCACTCCACTGACGATGTCCCACCAACATCCAGGAGGCGTTCTCCCAAGGACTTTAAAGCAA    2481

ATAAAACATATATTGTTCAGAAAAAAAAAAAAAAAAAAA
```

TSC2
TSC2 is a novel 1863 bp gene fragment. The nucleic acid was initially identified in a cloned fragment having the following sequence:

```
                                                                     (SEQ ID NO: 2)
  1 AAGCGTGACCCTAAGTCTAGCCTGGAGCCAGGGCTAGAGTGGTCATTTCTTTGTGGGTGCTGCCAGGGAGGGGCCAGAC    81

CCACAGGCTACTCAAAGGGCCTAGAGACCCCTCCCCAGGCAGGTGCTGCCCCAGGAGGAGCATGTCCTGGGGTCCGGGA   161

CTGAAGTCCATGTGGCCTCAGCCCCCCACACCCAGAACACCGCTTGCCTAAGGTGCTTTTGGCTTTAGTGTGTGATGTTT  241

GCTGTGCTTCTGGGCTGAATTAGCTTCCAAATCAGGACCTGGAGCCTCTACCCTGGCCCAGCCAGCCAGTGTGAGCTCTG  321

GTCTGTGAGATGGGCAGCTACGGGCCAGTGGAGCAGCATGTGGTGGGAGGGGCAAGGCTGGGACCCAGTGGTTTACAGAC  401

CTGTGGCCCTCCTGGAGCAACCTGGCAGCTACGGATCCCAGAACCCCCTGGGCTTCAGCTCCCCAGAGGGGAGAGGCTC   481

CACGTTGCTTTCCTTCCCCAAAATCCCTTTCTTTGTGCTGGTGTCTGGGACCAAAAGGAGTGGGCAGAGGACTCGGAGGG   561

CCTAGGGGTCCCAGTCGGGGCATCTGTAGCTCCTAAGCACGACAAGCATCAGTGCAGGGGACCCTGGCCTTGACTCCAAC   641

TGGCCTGGCGCCAGGAACCTCCAGGGCCAGAGCAGCCCAGCTGCAGCCAGCCTGCCCACTATGGGTATGTTCCTGGCCTA   721

AGGTCCGGAGGGAGGTTTGGGGTATCCCTGCCTGGGTGCCTGGGTGTGCCCTGGGGCCTCTCAGAAGCACAAATGCTGCC   801

CCCTGGCCGTGAGCAGGCCACAAGGTGAATGTATATAGCATGAGAGGCGGGCACTGCCCAGACGTGGCTGTGAACTTGTG   881

CTGTCTCGGGAGTCCTGACCTTCTGTGCGTGAGTGCCCCCATCTGTGACGTTTCACTCACCGAGGCTGAAGAAAGGAAGC   961

AGGGGAAATGAAAGCAGGGGTTTCTCGCCCTGACCCCTGCGGAGGAGACGGCTCCTACCACTGCGGTTGGCTTCATTTCG  1041

TTTTCCTGATTTCTGGGGTGCCACTTACCTACTCAATCCCAGTGGTCCACCCCCACATCCCCAGGGAGTGAGCAGTCCAG  1121

TGCCAGCTGCCTGTGATTGGTCCCCAGTCCCTATTACCCAAGGGGACCCTACAGCTCTGGTGGGTAACAAGGAGGGCTAA  1201

GCCACCAAACCAGAGCCCGATCCCTTGCCGAGCCAGGAGGAGGGATCTGGCTGAGAAAACTGATAGGACTGGAGGCCCCC  1281

ACCCCAACCAACACTCTCTGGTTTATGTGAGTAGCAGAAGATCCCGGCCTGGAGCATCCTTCAAGCCCTTCTCCCTGTGC  1361

CCACCCCGCCCCCCCCCCCCCCATATCACTATGCAATTCTTGACCCCAGCTCCAAAGCTTGCCCTACCCGGTCCCAGCT   1441

CTGTCCGGCCCAGAAGGTGGCTAGCTGGTGGGCCACAGGTGACCAGGGTCTCTTTGTTT TTCATCACAGCGGTGGTGTGC  1521

CGCACCCTTCCTCCCATATGTGATTTTGTGAGATTGCCTCCCAGTTACGGTCCCTCTGCCTGCATCTGCCCCCAGTGGAC  1601

TATGTCATCTGAATCGAGCCAGCCCCAAGTTCCCCTCCAGCCTCTGTAGGGCATGGCTGTGTGTTACTGTTGCTGTGCT   1681

TTCATTTTTTAAACTGGGTTTGGGGTTTGATTTTTATTTCTGTGGGAACTTTATTTTTCTTGGCAAATAACTAAAGTTC   1761

TTGTCCATGTAATTTCTGTGGTCTCTATTCAGCTTGGGTTTCATGTTTTAAAATAAACAATTTTAAGAAACAAAAAAAA   1841

AAAAAAAAAAAAAAAAGC
```

TSC3

TSC3 is a novel 750 bp gene fragment. The nucleic acid was initially identified in a cloned fragment having the following sequence:

```
                                                                            (SEQ ID NO: 3)
CTTGTTTATCCTACTCGGGTAGTTTCCTACTAATTTCAAGACTAGTGTTAACATTCTAAGGTAGTTATCTTAGGGTAGAT    81

TCAAGGTTTTAGATGACTAACAGTTCAGATTTTCTGATCAATTTTTTAAACACTAGAGAATAAAAGTGTACTAGAGAATA   161

AAAGCAGCTTCATAGTTAATTCTCACCAATTGGCCCTTTGCTAGCTGCTGGCTTTAGGTACACATAGGATAATATGTGTC   241

CACGTTTCTACTTGGAACTGGTAAAAGTTGTCACTGGCTGGAAAATGGTATCTCTCTTGTATACAAGATGGTCCATTG    321

ACACTGGTACTTTATGAAGCAGTTCTTTGTTTGTTTGATTGAGCTCTCTTGAACCTTGTTCATCTTTTAGTTTTTGCTTG   401

GAATGGAATGGAACTGGTTTGAAGTTAAAGGAAATATTCATTTTGAAACTTGTTCATTTTGAAAGGAAATGCAAGTTTCA   481

AAATGAAAAATAAAATGAAAAAGGAAATAAATTATTGTCCCAGATGGTCACTTGAGTTTTAAAAAATGGCTGCACACAGT   561

AAAACTGCTAAAAACAAAAACTTACCTCATTATTGGTTTGCATCTTTTTTCAGCTACTAATTTTATACCAAAATGTTAAA   641

TATTTATATTGTTTGAGTTTCAATCTTGTATGGAAAAAAATAATTAGTAGGTCTAAAAATGCCATGCTTTCCAATAAAGA   721

AGTTAAAAAAATCATCAGTAATGTGAATTT
```

TSC4

TSC4 is a novel 281 bp gene fragment. The nucleic acid was initially identified in a cloned fragment having the following sequence:

```
                                                                            (SEQ ID NO: 4)
1 GGGCCCCTCCGTCTCAGAGCAACTATACCCTCTACCTCGGAAGGAGCAGCAGAGAGAGAAGCCACAGGCCACCAGGAGGC    81

CCAGCAAAGCCACCAACTATGGAAGCTTCTCAGCCACCCCACCTCCCACCCTCTGGGAGGTCAGCACAAGAGTTGTGGGC   161

ACAAGCCGTTTCCGGGACAACCGGACAGACAAACGGGAACATGGCCATCAGGACCCAAATGTGGTGCCAGGTCCTCACAA   241

GCCAGTAAAGGGGAAGCTGCCCAAAAAGAAGGACAGAATTC
```

TSC5

TSC5 is a novel 1568 bp gene fragment. The nucleic acid was initially identified in a cloned fragment having the following sequence:

```
                                                                            (SEQ ID NO: 5)
1 CGCGCGGGAGCCAAGATGCCTCGCGGGGACTCGGAGCAGGTGCGCTACTGCGCGCGCTTCTCCTATCTTTGGCTCAAGTT    81

CTCTCTCATCATCTACTCCACCGTGTTCTGGCTGATTGGGGGCCTGGTCCTGTCAGTGGGGATCTACGCAGAGGCAGAGC   161

GGCAGAAATACAAAACCCTGGAAGAGTGCCTTCCTGGCCCCCGCCATCATCCTCATCCTCCTGGGGGTGGTCATGTTCAT   241

CGTCTCCTTCATCGGGGTGCTGGCTTCCCTCCGGGACAACCTGTGCCTTCTGCAGTCGTTTATGTATATCCTGGGGATCT   321

GCCTGGTCATGGAGCTTATTGGTGGGTCTGTATTTAGGGGCCGCCGGAACCAGACTATTGACTTTCTGAACGACAACATC   401

CGGAGAGGAATCGAGAATTACTACGATGATCTGGACTTCAAGAACATCATGGACTTTGTTCAGAAGAAGTTCAAGTGCTG   481

TGGCGGGGAGGACTACAGAGACTGGAGCAAAAACCAGTACCATGACTGCAGCGCCCCCGGGCCCCTGGCTGACGGGGTTC   561

CCTACACCTGCTGCATCAGGAACACGATGTTGTCAACACCATGTGTGGCTACAAAACAATCGACAAGGAGCGCCTGAATG   641

CACAGAACATCATTCACGTGCGGGGCTGCACCAACGCCGTGTTGATATGGTTCATGGACAACTATACCATCATGGCGGGC   721

CTTTTACTGGGCATCCTGCTTCCTCAGTTTCTTGGTGTGCTGCTGACCCTACTGTACATCACCCGTGTGGAGGACATTAT   801

CTTGGAGCACTCTGTCACGGATGGATTGCTGGGACCTGGTGCCAAGTCCAGAACGGACACAGCAGGCACTGGATGCTGCC   881

TGTGCTATCCCGATTAGCTATGCTGATTGAGCTATCCTGGCCCGGCACAGCAGCTCCCAGCCGGACTGTACTGCAAAGTG   961

CATCTAAGACTACACAAGCTGGACAGGACCAGCTGCAGCTCCTCTGCCCACCCACGGCGCTGACCAAAGCCCAGGGTGTA  1041

TGTACCTGCGTATAGTGTCTGATGGCCACTCCTCCTAGGGGAAAGCTGAACCCTGTGGGATCCCGGGAACAGGGATAGCC  1121

CAGCTCCGGTTCTGAGTCCTGGAGAAGGCAGCTCAGGGCTCCGTGTGGGCTCTTTTTCTTTCTGGCAGTGCCTTGGCCAG  1201
```

TSC6

TSC6 is a novel 300 bp gene fragment. The nucleic acid was initially identified in a cloned fragment having the following sequence:

```
                                                      (SEQ ID NO: 6)
  1 gccggctctt tgtggaggac tccatccatg accagtttgt gcagaaagtg gtggaggaag 61 tagggaagat gaaaatcggc gaccccctgg acagggatac caaccatggc ccgcagaacc 121 atgaggccca cctgaggaag ctggtggagt attgccaacg tggtgtgaag gaaggggcca 181 cactggtctg tggtgggaac caagtcccaa ggccaggctt cttctttcag ccaaccgttt 241 tcacagacgt ggaggaccac atgtacatcg ctaaggagga gtccttcggg cccatcatga
```

TSC7

TSC7 is a novel 965 bp gene fragment. The nucleic acid was initially identified in a cloned fragment having the following sequence:

```
                                                                    (SEQ ID NO: 7)
  1 CCCACAGCTCCTGCCCACTCACCAGGTCCAGGGGAGAGCAGGCGGTGACTCGATGACAAGTGCCTTTAGTTGAAGAGCAC  81

ATCTCACTCATTCCTCTCTCAGTACCTGATACATTCCTCTGTGCTAACCCCCCCTTGGGGAGGACCCACCCTCTGGAGGC  161

TGGACTTGGGGCGAACAGGCACTCACCTGTCACTGCCAAGGGCGGGCAGGCCATCCTTCCGAGCCCATGGGAGCCGGGAC  241

CACTAAGACTGCTGGTGGGAAGAAGTTGGGTGCTGGGCTGATGGTCTTGCTTTCTCTTGGTCTTCGCTTGTAATGTGGCT  321

GGCCCATGTTGGTTTTATGTTTAATGCTGTGCTTATAATAAGAAAGAGCCCCCCAAGCTGTACATTTATAAAAGTGAT   401

CATATACTGTATATAGAAAAATCTAGAAGCACATATGAATGCAGCAGGTAGTATTCCACTGTACCCATTCATGAAGGTAG  481

GTTTTATTACAGGACTCGCACCAGGTACTTACAGACGCGCCCTCTCCTCTTTGCCTAGAGAAACAGTCACTGCATTCCCG  561

CACAGTCCCTCAGACCCCCTTACCCTCTTCCCTGTAGGAAATTCTCCTGTGACCCCTCTGCCGTCCTCCCTTACTTCCTA  641

AATAAATGTAACGGAGTCAGTGCAAAAAAAAAAAATAAATGACATTTATTGTGGGTTATAATTTTCTCCTAAAAACAAA  721

ACCAGTGGTATGGTCATACCCACCATTGTTTCCCCACTTTCCATGACCGTCACAAACATCTGGGATGAGCACCTTGTGAG  801

CAGGAAAAGTTATGCTTTAAGAAATTTCTGGCCAGGCGTGGTGGCATACACCTTTAATCCCAGCACTCGGGAGGCAGAGG  881

CAGGTGGATTTCTGAGTTCGAGGCCAGCCTGGTCTACAAAGTGAGTTCCAGGACAGCCAGGGCTACACAGAGAAACCCTG  961

TCTCG
```

TSC8

TSC8 is a novel 408 bp gene fragment. The nucleic acid was initially identified in a cloned fragment having the following sequence:

```
                                                      (SEQ ID NO: 8)
  1 gccgggtctg aaaaggacta ggctggcatt ggtgacaccg agcttgttgg cagccacaca 61 ggtatagttg ccatagtgtt cctcagtgac attggtcacc gtcagggagg actggccctc 121 agtgctctta atctcaaggc catttgcact gtttatcctg gtgtcatccc ggtaccactc 181 aaagtcaggt gcaggcaccg ctgaggcttc acatttgagg gaagcttgtc gtcctgtggt
```

```
241 ggcttcgttg ctcttcgact ccgtgatagt gggtggatag ttcacagtga ccttgacttg 301 tttgacatcc gccgaggaga cctcgttggc agccttgcac tcatatttgc ctgactgttc 361 cctggtgatg cctaggatct ccagatattc ttcttctcct tcaaatty
```

TSC10

TSC10 is a novel 354 bp gene fragment. The nucleic acid was initially identified in a cloned fragment having the following sequence:

```
                                                                   (SEQ ID NO: 9)
  1 gtgcaccaga tgttctacga ggcccta-
gat aagtacggga acctcagtgc tctgggcttc 61 aagcgcaagg acaagtggga gcg-
tatctct tactgccagt actacctgat tgcacgcaaa 121 gtagccaaag gcttcttgaa gctcggc-
cta gagcgtgccc acagcgtggc gatccttggc 181 ttcaactctc cagaatggtt cttctctg-
ca gtgggcacag tgttcgcagg gggcattgtc 241 actggcatct acaccaccag ctccccg-
gag gcctgccagt acatctctca tgactgccga 301 gccaatgtca tcgtggttga cacacagaag cagctggaaa agatcctgaa gatct
```

TSC11

TSC11 is a novel 955 bp gene fragment. The nucleic acid was initially identified in a cloned fragment having the following sequence:

```
                                                                              (SEQ ID NO: 10)
1 CGGATCATCTGGGTCGCGACCTTGAGGCCGGGAATCGAGTTTCCAAACGTGCGGGGCCTTCGCCGGCTCTGCTGCCCCC    81

TTTCTCTCCATGGCAGCGGCCCGGAACCTGCGCACCGCGTCATATTCGGAGGCTTCATCTCCATGGTCGGCGCCGCCTTC   161

TATCCCATCTACTTCCGGCCCCTTATGCGGCTGGAGGAATACCAGAAGGAGCAGGCTGTAAATCGAGCTGGTATTGTCCA   241

GGAAGATGTGCAACCGCCAGGTTGAAAGTGTGGTCTGATCCATTTGGCAGGAAATGAGGCTGTCAGCAAGTCTGATGAGG   321

AAAGTGGACGTCTTTATCCTGTGCACTCCGCAGTGGGGACAATAGATGCCTCACTGTGGCAGCATGGCATGGAGAGGGAA   401

CTCTCATGCTGCTAGCCAGACCCCTTGTGATAGAGACTGTGTGCAAAGACAGTGCTTCCCTTAACTCCCTGGAGAACCTG   481

AACAGATGCCACCATTAGGAAGTGCCTTGCGGCTCCATTGACTTTGCAGGAGCAGAGCCAGCCTGCAAGGCTGTTTGTGG   561

AAGATCTGCTGCTCCTGCAGTCTTTATCACTTCCAAGCTGTGATGTGAACACAAGCAACCTGTGGGCTCAAGGTCCGTGG   641

CTGCTCTGACACCTTTTGAATAAGCGATTTCAGTGCAAATGGCCTTGCCAAGCTGCCTCGCAGGGTTCTTGGAGGATGTT   721

TCAGTTGATAAAACTGTTTGAAGACAGGATCCTTGGCACTGTTTAAGAATATACACTGCTCAGCTTAACCATTTCATTGA   801

AAGTCACTGTGTGTGGAAGTGAATAGGGAGCGAGTCACACTAGACTATACCACACACAGTAGATTCCTGCGTGAGGCTGC   881

AGGTATTAAAATGGTTTCTCTTAAAAAAAAAAAAAAAA
```

TSC12

TSC12 is a novel 1113 bp gene fragment. The nucleic acid was initially identified in a cloned fragment having the following sequence:

```
                                                                              (SEQ ID NO: 11)
1 GGAGACCCAAGATCTGAACCAGCCAGCCAGGTGCTGCACAGCCTCAACTTTGGGAGCAGAGGCCCTGTGGGGTTAACTTG    81

GGTCTGCCAGAAACAGTGCTTCCCGCAGGGAAAATCTTGGGTCAAGATGGAGGCTGCTCTGGAACACTGAGTGTTTCAAG   161

GGAGAAAGAGTGGGAACCGTGGCCCTTTGGGGCCAGACCCTGCAGGAGCTTGCCTCGCCTTTGAGGAGGAGGCACTGCTC   241

TTCAGGTGCCCTGGAGGGGCTTTTAGTGCCATCCCCACAGCAGAGTAAAGGTGGCGCGTATGTCATCGGGTGGCTTTGCG   321
```

-continued

```
CTGGTAGAACGCTGTTCTCTACCCTGCTGCAGCCTTTCACACTCACACACACCCAAACACACACTTCTCGGCCCTGTATG    401

TTCAGGTGAGAGACAAGGGAAGATGGCTCATCATTTTCAGCCATGTCCCCAAAGTGGCCTCTCTTTCATGCTCTGTGGGC    481

TTTGGCCTGCAGCTGTTCCAGAGTTAGGGATGTGATTTTTGTCTGTGAGGTACCCCTTGCCCTAGTGGATCAGTTACAGG    561

CCTATGTCCAGCACCAGAGTCCCTGTTCCGATATCATCACAGATAGCCTGTTGTTTTCCACAGAGGAGCCAGATGTAAGT    641

CAGACACCTCCAGCCTACCAGTCTCCTGCCATCAGCTTTGGCTCTAATGGGCTCTTGGTGGCCTCCTTGGTGTGTCACTG    721

GTACAGGACAGCAAGTGGCTCAGAAAGGCTGCTTGCTCCTGAGCTCAGCCACTTATTCACATGGTTCAGAGCAGATCTTT    801

GTACTCTTCAGACTCAAGTATGGTGATCTGTTTGACAGTAGAGGTCTGGCCTACCCCTCACCCTCATTCTCCAGCACCTC    881

TAACAAGAACCACACTCATGCCTCTGGTGTCAGTTTTCTTGTCTGCCTTCCCTGGCCTACCTAGATATTTATTTCTTGTG    961

TTTTATGAATAGTTAAGCCCTGCCCATCTGTGCCTTTCAGACGGAAACACAGAAACCTAGGCTGTGCCATTTGTCTTCTC   1041

ACAGTTGTTTAATGAAACCTCAAGGAATATGGAAATAAAGCCTAGACCCTGGAGTGGTGAAAGAGTAAAAAAA
```

TSC15

TSC15 is a novel 594 bp gene fragment. The nucleic acid was initially identified in a cloned fragment having the following sequence:

```
                                                                      (SEQ ID NO: 12)
1 AGATCTCTGTTTCCTCTTTCTTCTCTCCTCTATGCTCTTCTGTAGCCTACCCTCAGGGTGATCTCTAACCCAAACTAATC    81

CCGAGGAACAGACACTTGGCTCAGCTCCACCTACTACCTGGCTCACCTGTTCCCAGAATCTCCATAGAAGAGGGCACTTT   161

CTTTCTCAAGTTACCCTAACATTCTCTGCAGGATAAAATCATGAGTCCAGCCTGTCTGTGGAACTGGGGCCTGTCTGCAG   241

CTTCCCTGCAGAAGTGTCCATTCACTTTGGGTGATCTTCCCGACCAAGATACTTAGGTGTTTTGGCCAGCACCAGTATTT   321

CTATGAATTCCTGATCTGGAGTTGAATAGACAGGAATCAAGACCTAGGCTTTTCACTGTGTGAACCTGAGCATGTGGCCT   401

GACCTGCTGGAAGCTCCTCTGCTCTTGTGTGAAGCAGGAATGCTGTCAGGCACACAGCACAACACACCAGTGGTGGAGAA   481

CGCTAATCCCAACACACAAATTCCACAGAAATGGCACTATCCTCGGGTCTCCTGCCTAACCATGGACAAAGCTGAGAATA   561

AACAGTGCTTTACTTTGAAAAAAAAAAAAAAAAA
```

TSC16

TSC16 is a novel 713 bp gene fragment. The nucleic acid was initially identified in a cloned fragment having the following sequence:

```
                                                                      (SEQ ID NO: 13)
1 CAATTGTTTTTTCTAACCATCTTAGGGAACAATACATTGCAATAATTGATAATAGTGCCATCACTGTAATAAACTTTAGA    81

GACTTTTTTAATGTAAAAGTTGTTGGTCACCTTGTTTCCTGTAACCTTCACTCTGTCACACGAGTTGGCTCATAGGTTG   161

TGTTTGTCTATCAGAAATAAGAAAAACACAAGTGAAGAAAATGTTGGCATGAAGTCATCCATCTGCAATGAAAAACCTAA   241

AAGACTACGGGTCACTCATGTTATCAATATAATTTATAATCCTGTTCAGTGTACAAAATTGTGGGTTTTGTACTCACCCA   321

AAAGACTAAAACACCAGTTTTTCTTACAGTATCTATCTACAGAGCTTATTCTCCCCTATTATTTGGGAAACTCTGAGACT   401

CCATATTGCAGAAGTCAAGGAATAGGCCATATAAGAAAATGTAGCTTGTTTTTATTATTTCTGCATATTTATTTCTAGAT   481

CTTGGGCTCATTTGTTAACAGAATAAGTTGTCAAAGGTAAAGTCCTTGAGTCTGGGAATGAGCCATCGTTCCAAAACCAA   561

CACACCCTGTGTGGAAATTTTACTTGACTCTGTTTTGCTGCATAGAATTCAGTGTCTCTTGGCCATTCCCCCTCATTCCT   641

ATACTAAATTCTTTGAAGACACTGGTAACAGTTTGTGGTAGACTACAGTTGAAAAAACTCAATCCTTATTTCT
```

TSC17

TSC17 is a novel 306 bp gene fragment. The nucleic acid was initially identified in a cloned fragment having the following sequence:

(SEQ ID NO: 14)
```
  1 ggatccctcc accctatgac aagaaaaagc ggatggtggt ccctgctgct ctcaagggtt
 61 gttcgcgctg aagcctacca gaaagtttgc ttacctgggg cgtctggcgc atgaggtcgg
121 gtggaagtac caggcagtga cagccactct ggaggagaaa cggaaggaaa aggccaagat
181 gcactatcgg aagaagaagc agatcttgag gttacggaaa caggcagaaa agaatgtgga
241 gaagaaaatc tgcaagttca cagaggtcct caagaccaac ggactcctgg tgtgaaccca
301 ataaag
```

TSC18

TSC18 is a novel 66 bp gene fragment. The nucleic acid was initially identified in a cloned fragment having the following sequence:

(SEQ ID NO: 15)
```
 1 gaattcgaat cacgctcacc agccgcaacg tgaagtcgct ggagaaggtt tgtgcggact
61 tgatca
```

TSC19

TSC19 is a novel 1613 bp gene fragment. The nucleic acid was initially identified in a cloned fragment having the following sequence:

(SEQ ID NO: 16)
```
   1 CCAGCTCAGAGGTTCTAGGGGCAGCCGGCGCGCTTCTCTAGTTGCAGCTTGGGCGGCTCCTGTGGTGGGCGGCTAGGGGC    81
     GAGCCGGGATGGGCTATAGACGCGCGACGTGATCAGTTCGCACGCGGACCCACGCCTCCCATCGCTCTGCCTCAAGAGCC   161
     TATTCTGTGGGTGCAGGCACGCACCGGACGCAGACCCGGCCGGAGCATGCGGGGTGCGGTGTGGGCGGCCCGGAGGCGCG   241
     CGGGGCAGCAGTGGCCTCGGTCCCCGGGCCCTGGGCCGGGTCCGCCCCCGCCGCCACCGCTGCTGTTGCTGCTACTACTG   321
     CTGCTGGGCGGCGCGAGCGCTCAGTACTCCAGCGACCTGTGCAGCTGGAAGGGGAGTGGGCTCACCCGAGAGGCACGCAG   401
     CAAGGAGGTGGAGCAGGTGTACCTGCGCTGCTCCGCAGGCTCTGTGGAGTGGATGTACCCAACTGGGGCGCTCATTGTTA   481
     ACTACGGGCCCAACACCTTCTCACCTGCCCAGAACTTGACTGTGTGCATCAAGCCTTTCAGGCACTCCTCTGGAGCCAAT   561
     ATTTATTTGGAAAAAACTGGAGAACTAAGACTGTTGGTGCGGGACATCAGAGGTGAGCCTGGCCAAGTGCAGTGCTTCAG   641
     CCTGGAGCAGGGAGGCTTATTTGTGGAGGCGACACCCCAACAGGACATCAGCAGAAGGACCACAGGCTTCCAGTATGAGC   721
     TGATGAGTGGGCAGAGGGGACTGGACCTGCACGTGCTGTCTGCCCCCTGTCGGCCTTGCAGTGACACTGAGGTCCTCCTT   801
     GCCATCTGTACCAGTGACTTTGTTGTCCGAGGCTTCATTGAGGACGTCACACATGTACCAGAACAGCAAGTGTCAGTCAT   881
     CTACCTGCGGGTGAACAGGCTTCACAGGCAGAAGAGCAGGGTCTTCCAGCCAGCTCCTGAGGACAGTGGCCACTGGCTGG   961
     GCCATGTCACAACACTGCTGCAGTGTGGAGTACGACCAGGGCATGGGGAATTCCTCTTCACTGGACATGTGCACTTTGGG  1041
     GAGGCACAACTTGGATGTGCCCCACGCTTTAGTGACTTTCAAAGGATGTACAGGAAAGCAGAAGAAATGGGCATAAACCC  1121
     CTGTGAAATCAATATGGAGTGACTTGCAGGGTGACACAGTACTGTTGTCCTTCAGATGAGCCATGTTTTGTGGGCTCAGT  1201
     CGCTCTATCATATCCTGATAGAGATTGCAGACTGGTGGCATGGGCCCAGCCTGGTGCTAGAACTGGGAAGGTACATGCTG  1281
     TTCTGACCCCTTAGGTCCCAGCCAAGGATGCCCTGACCCATTGGAACTGCTGTAAAATGCAAACTAAGTTATTATATTTT  1361
     TTTTGTAAAAGAAAAAAAAAAAAAAAAAAAGAAAACTCCGCGCACAGGGGGGGTACGTCCCAATTCGCCAAAAACAGATGC  1441
```

-continued

```
TAGAACCCCTGGCGGCCCCCCACCCCCACGGGAGACACTAGCTAACCAATTAATGCTTGGAAAATCCCTTCTGCACCGG    1521

TAGTACGAAAGGCCCACGATGCCTTCAAAGCTGCCTGGACGGAATGCAAATGAACGCTAATTTCTAATCCGGTAATTGTA   1601

ACCGCATTCTACA
```

TSC20

TSC20 is a novel 2245 bp gene fragment. The nucleic acid was initially identified in a cloned fragment having the following sequence:

(SEQ ID NO: 17)
```
1 ACGTGACCGTGAGACCCTAGGAGCAATGGCGGGGCGGCTGGCTGGCTTCCTGATGTTGCTGGGGCTCGCGTCGCAGGGGC     81

CCGCGCCGGCATGTGCCGGGAAGATGAAGGTGGTGGAGGAGCCTAACACATTCGGGCTGAATAACCCGTTCTTGCCCCAG    161

GCAAGCCGCCTTCAGCCCAAGAGAGAGCCTTCAGCTGTATCCGGGCCCCTGCATCTCTTCAGACTTGCTGGCAAGTGCTT    241

TAGCCTAGTGGAGTCCACGTACAAGTATGAATTCTGCCCTTTCCACAACGTCACCCAGCACGAGCAGACCTTCCGCTGGA    321

ATGCCTACAGCGGGATCCTTGGCATCTGGCATGAGTGGGAAATCATCAACAATACCTTCAAGGGCATGTGGATGACTGAT    401

GGGGACTCCTGCCACTCCCGGAGCCGGCAGAGCAAGGTGGAGCTCACCTGTGGAAAGATCAACCGACTGGCCCACGTGTC    481

TGAGCCAAGCACCTGTGTCTATGCATTGACATTCGAGACCCCTCTTGTTTGCCATCCCCACTCTTTGTTAGTGTATCCAA    561

CTCTGTCAGAGGCCCTGCAGCAGCGCTGGGACCAGGTGGAACAGGACCTGGCAGATGAACTGATCACACCACAGGGCTAT    641

GAGAAGTTGCTAAGGGTACTTTTTCGAGGATGCCGGCTACTTAAAGGTCCCAGGAGAAACCCATCCCACCCAGCTGGCAG    721

GAGGTTCCAAGGGCCTAGGGCTTGAGACTCTGGACAACTGTAGAAAGGCACATGCAGAGCTGTCACAGGAGGTACAAAGA    801

CTGACGAGTCTGCTGCAACAGCATGGAATCCCCCACACTCAGCCCACAGAAACCACTCACTCTCAGCACCTGGGTCAGCA    881

GCTCCCCATAGGTGCAATCGCAGCAGAGCATCTGCGGAGTGACCCAGGACTACGTGGGAACATCCTGTGAGCAAGGTGGC    961

CACGAAGAATAGAAATATCCTGAGCTTTGAGTGTCCTTTCACAGAGTGAACAAAACTGGTGTGGTGTAGACACGGCTTCT   1041

TTTGGCATATTCTAGATCAGACAGTGTCACTGACAAACAAGAGGGACCTGCTGGCCAGCCTTTGTTGTGCCCAAAGATCC   1121

AGACAAAATAAAGATTCAAAGTTTTAATTAATTCCATACTGATAAAAAATAACTCCATGACTTCTGTAAACCATTGCATA   1201

AATGCTATTGTAAAAAAAATTAAACAAATGTTAACAACTTTAACAATTCACTAAAGTAAATGGTTATGTATTATAAATAT   1281

GACCATCTGGGTTAAGAAGATTCCATTCACATAACATTCTCAACTAATTTCTGAAGAACAAATGAACACAAAGGCTTCCA   1361

TAAGTTAATCCACATGCGCATCCATACTGGGGAAGGCCTGCCAACCAGGTACACAAGACTCTGACACTACCATATACTG   1441

TTACTATTCAACACTAGAGAGTTAGACGACAACAGGCATCAGGACAGTGGTGGGTCCCAGTTCCTAGACCCATGGCCCCA   1521

CCTCCATTACCCACACACGGGCCTTAAGGCTCTCTCTCCCCTTCTTGGCCCTTCCCACCCAGGGTAGATCCTAGAAGCCT   1601

CAGCTCCTAAGAGGTCTGGAATGGATGGGAAAAGTGGCCCCTTCTGGGACGTTCTTTGGTCCTCCCCTGCACACCTGTCC   1681

TCAGAGCTCAGCCTGATTCCAGAAGAGCAGATGCTCAGGAAAGCTCCCCGCATGGGATGGGACCCAGGGTGCACTACCGC   1761

CTGCCTCCCCAGCCATCACAACAGCCCCAGAACTGCCCAGCCCCAGCCTGGAATGTCAGCCCAGGAGGAGTTAACCAGAG   1841

TAGCTTACATACAATCTAAAGCTTAATGTAACTGTATACAACTTGAAATTGTCCCGATGAGCTATCAATCACAAACACTG   1921

TCCTGTTACCACAGAGACCAAAAGCCTGACATGGGAAACAGTTCATAAATATGAATAAAAATAAACAATCTTAAACCATG   2001

GTAACAGTAGCACCAAATACACATGATCTAGGTACTGAGCTAATAAATCATTATCACTATAATTAAAAACAAAAGTCACT   2081

GAAATCAGGTCAATAGTTACCTTATTAAGTAGTGGGCTAGCTGTGGAATGTTGAAGATCCATTTCCTTTAAAATGATATA   2161

GGTCTTTTCTATCAGTTTGTCTTATATTAAAAAATGCTTTTAAATTTCCTACTATATTAAATACATTCTAATTTGGTCAC   2241

TGATA
```

TSC21
TSC21 is a novel 171 bp gene fragment. The nucleic acid was initially identified in a cloned fragment having the following sequence:

(SEQ ID NO: 18)
```
  1 actagtcacc aaaatgcttg gt-
tctaagtg gtagagaagg agacacctta gatataatac 61 aggt-
caactt tttgacgtgg ggtggggtg ggggtggggg tgggggtgaa catcacggtc 121 gcaaataagc agggtttgag ctttgtccag attgtagact taataaaatt y
```

TSC22
TSC22 is a novel 491 bp gene fragment. The nucleic acid was initially identified in a cloned fragment having the following sequence:

(SEQ ID NO: 19)
```
  1 CAGTTGCAGAAGGGAGAAATCACGGCA-
GAATCATCGAGAAACCTGAAAAATGAGACCTAGAATGAAGTATTCCAACTCCA

81 AGATTTCCCCGGCAAAGTTCAGCAGCAC-
CGCAGGCGAAGCCCTGGTCCCGCCTTGCAAAATAAGAAGATCCCAACATAAG

161 ACCAAAGAATTCTGCCATGTCTACTG-
CATGAGACTCCGTTCTGGCCTCACCATAAGAAAGGAGACTAGTTATTTTAGGAA

241 AGAACCCACGAAAAGATATTCAC-
TAAAATCGGGTACCAAGCATGAAGAGAACTTCTCTGCCTATCCACGGGATTCTAGGA

321 AGAGATCCTTGCTTGGCAGTATCCAAG-
CATTTGCTGCGTCTGTTGACACATTGAGCATCCAAGGAACTTCACTTTTAACA

401 CAGTCTCCTGCCTCCCTGAGTACATA-
CAATGACCAATCTGTTAGTTTTGTTTTGGAGAATGGATGTTATGTGATCAATGT

481 TGACGACTCTG
```

TSC23
TSC23 is a novel 659 bp gene fragment. The nucleic acid was initially identified in a cloned fragment having the following sequence:

(SEQ ID NO: 20)
```
1 ATTTGGAATTTTAAGTTTTATCAATGCTTCTGGAAGCTTAGAACTGTACACGTGTGATGTCAGTCACATAGAGGAATGTG   81

CCCGGACTGCCTCATGCCTTTATTTTCCTTGGTAAATTTGAAGATAGAATGTCTGACTAGCGCAGTGACCAGAAAACAAT  161

GTGGTAGTCAACATCTCAGGCCATATTTTAAGATCCTGTAGAGCACTATTCATTTCAGGTTGCAGATGGAGTATTTTGA   241

AACATCATTACTATGTAGATGCTTGGATAGGAGTGAGGGGGAGCTAGCAGATTTCCTGTGCCATTTATTCAGCTGATTGA  321

TGTACAGATGTAGGTTTATTTTGTAAAATCCACTGAAAGAATATGGCCACACCCTTGCCTACTTGATAGCATCAATACAG  401

AAGCCAAGAAGGACCACTAAGTAACCCCCTCTTCCCAGGGAGAGCAGCTAGCTTGAAATCTCTCGGATACAATCGATGCG  481

TCTGACCTTTGGGATCCTCACCATATGGGCAAACAATGGGCTTTGCAGGATGAGAGACACCCACTTAAACCTCTGACGAT  561

CTCGAATGGTTCATCTCTTCCGTCATTAACCAGTCATGGAAAACAATCAACAAACTCTGCCACGTGAAATATTTTTCAG   641

ACTTTTCTAACCCAAGCTT
```

TSC24
TSC24 is a novel 341 bp gene fragment. The nucleic acid was initially identified in a cloned fragment having the following sequence:

(SEQ ID NO: 21)
```
  1 raattcaaac aaagctttgg acaaggc-
ccg gttaaaaagc aaagatgtca agttggcaga
```

-continued
```
 61 gactcatcag caggaatgct gcca-
gaagtt tgaacagctt tctgaatctg caaaagaaga 121 gctgataaac ttcaaacgga agagagtg-
gc agcatttcga aagaacctaa tcgaaatgtc 181 tgaactggaa ataaagcatg ccagaaa-
caa cgtctccctg ttgcagagct gcatcgactt 241 attcaagaac aactgacctg tctactct-
ga aggacaccaa tgtgaaagcc agcatcactt 301 gcacttaaat cattactgca aaagaaatag ctttgactag t
```

TSC25

TSC25 is a novel 53 bp gene fragment. The nucleic acid was initially identified in a cloned fragment having the following sequence:

```
                                              (SEQ ID NO: 22)
  1    ggatcctgca aggctttggc cagctcagaa gcggcaaccc ctacacacct agg
```

General Methods

The TSCX nucleic acids and encoded polypeptides can be identified using the information provide above. In some embodiments, the TSCX nucleic acids and polypeptide correspond to nucleic acids or polypeptides which include the various sequences (referenced by SEQ ID NOs) disclosed for each TSCX polypeptide.

In its various aspects and embodiments, the invention includes providing a test cell population which includes at least one cell that is capable of expressing one or more of the sequences TSC 1-142. By "capable of expressing" is meant that the gene is present in an intact form in the cell and can be expressed. Expression of one, some, or all of the TSCX sequences is then detected, if present, and, preferably, measured. Using sequence information provided by the database entries for the known sequences, or the sequence information for the newly described sequences, expression of the TSCX sequences can be detected (if present) and measured using techniques well known to one of ordinary skill in the art. For example, sequences within the sequence database entries corresponding to TSCX sequences, or within the sequences disclosed herein, can be used to construct probes for detecting TSCX RNA sequences in, e.g., northern blot hybridization analyses or methods which specifically, and, preferably, quantitatively amplify specific nucleic acid sequences. As another example, the sequences can be used to construct primers for specifically amplifying the TSCX sequences in, e.g., amplification-based detection methods such as reverse-transcription based polymerase chain reaction. When alterations in gene expression are associated with gene amplification or deletion, sequence comparisons in test and reference populations can be made by comparing relative amounts of the examined DNA sequences in the test and reference cell populations.

Expression can be also measured at the protein level, i.e., by measuring the levels of polypeptides encoded by the gene products described herein. Such methods are well known in the art and include, e.g., immunoassays based on antibodies to proteins encoded by the genes.

Expression level of the TSCX sequences in the test cell population is then compared to expression levels of the sequences in one or more cells from a reference profile. Expression of sequences in test and control populations of cells can be compared using any art-recognized method for comparing expression of nucleic acid sequences. For example, expression can be compared using GENECALL-ING® methods as described in U.S. Pat. No. 5,871,697 and in Shimkets et al., Nat. Biotechnol. 17:798-803. In various embodiments, the expression of 2, 3, 4, 5, 6, 7, 8, 9, 10, 15, 20, 25, 35, 40, 50, 100, 150 or all of the sequences represented by TSC 1-142 are measured. If desired, expression of these sequences can be measured along with other sequences whose expression is known to be altered according to one of the herein described parameters or conditions.

A reference profile is an expression pattern derived from a single reference population or from a plurality of expression patterns. The reference profile can be a database of expression patterns from previously tested cells for which one of the herein-described conditions (e.g., tuberous sclerosis complex associated disorder) is known. Tuberous sclerosis complex associated disorders include for example, hamartomas, or hamartias in multiple organ systems, such as the brain, skin, heart or kidney, renal carcinoma, malignant angiomyolipoma, hypomelanotic macules, facila angiofibroma, shagreen patches and ungula fibromas.

In some embodiments, the test cell will be included in a cell sample from a subject known to contain, or to be suspected of having a tuberous sclerosis complex associated disorder. In other embodiments, the cell sample will be derived from a subject from a region known to contain, or suspected of containing, a primary tumor, such as a renal carcinoma. In further embodiments, the cell sample will be derived from a subject from a region known to contain, or suspected of containing, a metastasis of a primary tumor.

Preferably, cells in the reference profile are derived from a tissue type as similar as possible to test cell, e.g., brain, skin, heart or kidney tissue. In some embodiments, the control cell is derived from the same subject as the test cell, e.g., from a region proximal to the region of origin of the test cell.

In some embodiments, the test cell population is compared to multiple reference profiles. Each of the multiple reference profiles may differ in the known parameter or condition. Thus, a test cell population may be compared to a first reference profile known to have an tuberous sclerosis associated disorder, as well as a second reference population known not to have a tuberous sclerosis associated disorder.

In various embodiments, the expression of one or more sequences encoding genes of expressed in distinct gene profiles, as listed in Table 1, is compared. These gene profile include, e.g., "MEF and NSC –/– conserved differential expression" (such as, TSC 1-9), "MEF and NSC –/– opposite differential expression" (TSC 10-18), "NSC Only", (TSC 19-44), and "MEF Only" (TSC 45-57). In some embodiments, expression of members of two or more gene profiles are compared.

Whether or not comparison of the gene expression profile in the test cell population to the reference profile reveals the presence, or degree, of the measured condition depends on the composition of the reference profile. For example, if the profile is composed of cells that have an tuberous sclerosis associated disorder, a similar gene expression level in the test cell population and a reference profile indicates the presence of the tuberous sclerosis associated disorder in the test cell population. Conversely, if the reference profile is composed of cells that do not have an tuberous sclerosis associated disorder, a similar gene expression profile between the test cell population and the reference profile indicates the absence of the tuberous sclerosis associated disorder in the test cell population In various embodiments, the TSCX sequence in a test cell population is considered comparable in expression level to the expression level of the antileukoprotease sequence if its expression level varies within a factor of 2.0, 1.5, or 1.0 fold to the level of the TSCX transcript in the reference profile. In various embodiments, a TSC sequence in a test cell population can be considered altered in levels of expression if its expression level varies from the reference cell population by more than 1.0, 1.5, 2.0 or more fold from the expression level of the corresponding antileukoprotease sequence in the reference cell population.

If desired, comparison of differentially expressed sequences between a test cell population and a reference profile can be done with respect to a control nucleic acid whose expression is independent of the parameter or condition being measured. Expression levels of the control nucleic acid in the test and reference nucleic acid can be used to normalize signal levels in the compared populations.

The test cell population can be any number of cells, i.e., one or more cells, and can be provided in vitro, in vivo, or ex vivo.

In other embodiments, the test cell population can be divided into two or more subpopulations. The subpopulations can be created by dividing the first population of cells to create as identical a subpopulation as possible. This will be suitable, in, for example, in vitro or ex vivo screening methods. In some embodiments, various sub populations can be exposed to a control agent, and/or a test agent, multiple test agents, or, e.g., varying dosages of one or multiple test agents administered together, or in various combinations.

The subject is preferably a mammal. The mammal can be, e.g., a human, non-human primate, mouse, rat, dog, cat, horse, or cow.

Diagnosing a Tuberous Sclerosis Complex Associated Disorder

The invention provides a method of diagnosing or determining the susceptibility of a tuberous sclerosis complex associated disorder, e.g., hamartomas, or hamartias in multiple organ systems, such as the brain, skin, heart or kidney, renal carcinoma, malignant angiomyolipoma, hypomelanotic macules, facila angiofibroma, shagreen patches and ungula fibromas. A tuberous sclerosis complex associated disorder is diagnosed by examining the expression of a nucleic acid encoding a TSCX nucleic acid from a test population of cells from a subject suspected of having a tuberous sclerosis complex associated disorder. The population of cells may contain cells of the brain, or may alternatively may contain cells the eye, skin, heart, or kidney.

Expression of a TSCX nucleic acid is measured in the test cell and compared to the expression of the sequence in the reference profile. A reference profile can be a TSC disorder positive reference profile. By "TSC disorder positive reference profile" is meant that the reference profile contains cells derived from tissues with a tuberous sclerosis complex associated disorder. Alternatively, the reference profile can be an TSC disorder negative reference profile. By "TSC negative reference profile" is meant that the reference profile contains cells derived from tissues without a tuberous sclerosis complex associated disorder.

When a reference profile is an TSC disorder positive reference profile, a similarity in expression between TSCX sequences in the test population and the reference profile indicates the presence of a tuberous sclerosis complex associated disorder in the subject. Conversely, a difference in expression in the test cell population between TSCX sequences in the test population and the TSC disorder positive reference profile indicates the absence of a tuberous sclerosis complex associated disorder in the subject.

When the reference profile is TSC disorder negative reference profile, an difference in expression pattern between the test cell population and the TSC disorder negative reference profile indicates the presence of a tuberous sclerosis complex associated disorder. Conversely, a similarity in expression expression between TSCX sequences in the test population and the TSC disorder negative reference profile indicates the absence of a tuberous sclerosis complex associated disorder in the subject.

Methods of Treating Disorders Associated with Tuberous Sclerosis Complex

The invention provides a method for treating tuberous sclerosis complex associated disorders in a subject by administering to a subject in need thereof a compound that modulates the expression of one or more TSCX nucleic acids or polypeptides. Administration can be prophylactic or therapeutic to a subject at risk of (or susceptible to) tuberous sclerosis complex associated disorder. The tuberous sclerosis associated disorder can be, e.g., hamartomas, or hamartias in multiple organ systems, such as the brain, skin, heart or kidney, renal carcinoma, malignant angiomyolipoma, hypomelanotic macules, facila angiofibroma, shagreen patches and ungula fibromas.

The therapeutic method includes decreasing or inhibiting the expression, or function, or TSCX nucleic acids in the diseased cell relative to normal cells of the tissue type from which the diseased cells are derived. In these methods, the subject is treated with an effective amount of a compound, which decreases the amount of a TSCX nucleic acid or polypeptide in the subject. Administration can be systemic or local, e.g., in the immediate vicinity of, the subject's diseased cells. Expression can be inhibited in any of several ways known in the art. For example, expression can be inhibited by administering to the subject a nucleic acid that inhibits, or antagonizes, the expression of the TSCX. In one embodiment, an antisense oligonucleotide can be administered which disrupts expression of a TSCX nucleic acid.

Alternatively, the function a TSCX can be inhibited by administering a compound that binds to or otherwise inhibits the function of the TSCX gene products. The compound can be, e.g., an antibody to a polypeptide encoded by a TSCX nucleic acid.

These modulatory methods can be performed ex vivo or in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity TSCX proteins or nucleic acid molecules. In one embodiment, the method involves administering an agent (e.g., an agent identified by a screening assay described herein), or combination of agents that modulates (e.g., upregulates or downregulates) expression or activity of TSCX nucleic acids or polypeptides. In another embodiment, the method involves administering a protein or combination of proteins or a nucleic acid molecule or combination of nucleic acid, molecules as therapy to compensate for aberrant expression or activity of a TSCX nucleic acid.

Therapeutics that may be utilized include, e.g., (i) a polypeptide, or analogs, derivatives, fragments or homologs thereof of the overexpressed sequence; (ii) antibodies to the overexpressed sequence; (iii) antisense nucleic acids or nucleic acids that are "dysfunctional" (i.e., due to a heterologous insertion within the coding sequences of coding sequences of one or more overexpressed or underexpressed sequences); or (v) modulators (i.e., inhibitors, agonists and antagonists that alter the interaction between an overexpressed polypeptide and its binding partner. The dysfunctional antisense molecules are utilized to "knockout" endogenous function of a polypeptide by homologous recombination (see, e.g., Capecchi, Science 244: 1288-1292 1989)

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Administration of a prophylactic agent can occur prior to the manifestation of symptoms characteristic of aberrant gene expression, such that a disease or disorder is prevented or, alternatively, delayed in its progression. Depending on the type of aberrant expression detected, the agent can be used for treating the subject. The appropriate agent can be determined based on screening assays described herein.

Screening Assays for Identifying a Candidate Therapeutic Agent for Treating or Preventing Tuberous Sclerosis Associated Disorder The differentially expressed sequences disclosed herein can also be used to identify candidate therapeutic agents to treat or prevent tuberous sclerosis associated disorders. The therapeutic agent can be identified by providing a cell population that includes cells capable of expressing TSCX nucleic acids. Expression of the nucleic acid sequences in the test cell population is then compared to the expression of the nucleic acid sequences in a reference cell population, which is a cell population that has not been exposed to the test agent, or, in some embodiments, a cell population exposed the test agent. Comparison can be performed on test and reference samples measured concurrently or at temporally distinct times. An example of the latter is the use of compiled expression information, e.g., a sequence database, which assembles information about expression levels of known sequences following administration of various agents. For example, alteration of expression levels following administration of test agent can be compared to the expression changes observed in the nucleic acid sequences following administration of a control agent.

An decrease in expression of the nucleic acid sequence in the test cell population compared to the expression of the nucleic acid sequence in the reference cell population that has not been exposed to the test agent indicates the test agent is a candidate therapeutic agent.

The test agent can be a compound not previously described or can be a previously known compound but which is not known to be an agent for treating tuberous sclerosis complex disorders.

The invention also includes a compound identified according to this screening method.

An agent effective in stimulating expression of underexpressed genes, or in suppressing expression of overexpressed genes can be further tested for its ability to prevent the tuberous sclerosis complex associated disorders, and as a potential therapeutic useful for the treatment of such pathophysiology. Further evaluation of the clinical usefulness of such a compound can be performed using standard methods of evaluating toxicity and clinical effectiveness.

Selecting a Therapeutic Agent for Treating Tuberous Sclerosis Complex Associated Disorder that is Appropriate for a Particular Individual Differences in the genetic makeup of individuals can result in differences in their relative abilities to metabolize various drugs. An agent that is metabolized in a subject to act as a therapeutic agent can manifest itself by inducing a change in gene expression pattern from that characteristic of a pathophysiologic state to a gene expression pattern characteristic of a non-pathophysiologic state. Accordingly, the differentially expressed TSCX sequences disclosed herein allow for a putative therapeutic or prophylactic agent to be tested in a test cell population from a selected subject in order to determine if the agent is a suitable therapeutic agent in the subject.

To identify a therapeutic agent, that is appropriate for a specific subject, a test cell population from the subject is exposed to a therapeutic agent, and the expression of one or more of TSCX 1-141.

In some embodiments, the agent is first mixed with a cell extract, which contains enzymes that metabolize drugs into an active form. The activated form of the therapeutic agent can then be mixed with the test cell population and gene expression measured. Preferably, the cell population is contacted ex vivo with the agent or activated form of the agent.

Expression of the nucleic acid sequences in the test cell population is then compared to the expression of the nucleic acid sequences a reference cell population. The reference cell population includes at least one cell whose tuberous sclerosis complex status is known. By "tuberous sclerosis complex status is meant, whether or not the reference cell population contains cells known to have tuberous sclerosis complex subject.

The test agent can be any compound or composition.

Assessing Efficacy of Treatment of a Tuberous Sclerosis Complex Associated Disorder in a Subject The differentially expressed TSCX sequences identified herein also allow for the course of treatment of a tuberous sclerosis complex associated disorder to be monitored. In this method, a test cell population is provided from a subject undergoing treatment for a tuberous sclerosis complex associated disorder. If desired, test cell populations can be taken from the subject at various time points before, during, or after treatment. Expression of one or more of the TSCX sequences, e.g., TSCXs: 1-142, in the cell population is then measured and compared to a reference cell population which includes cells whose pathophysiologic state is known. Preferably, the reference cells not been exposed to the treatment.

If the reference cell population contains no cells exposed to the treatment, a similarity in expression between TSCX sequences in the test cell population and the reference cell population indicates that the treatment is efficacious. However, a difference in expression between TSCX sequences in the test population and this reference cell population indicates the treatment is not efficacious.

By "efficacious" is meant that the treatment leads to a decrease in the pathophysiology in a subject. When treatment is applied prophylactically, "efficacious" means that the treatment retards or prevents a pathophysiology.

Efficaciousness can be determined in association with any known method for treating the particular pathophysiology
Assessing the Prognosis of a Subject with a Tuberous Sclerosis Complex Associated Disorder Also provided is a method of assessing the prognosis of a subject with a tuberous sclerosis complex associated disorder by comparing the expression of a TSCX nucleic acid in a test cell population to the expression of the sequences in a reference profile derived from patients over a spectrum of disease stages. By comparing gene expression of a TSCX nucleic acid in the test cell population and the reference profile, or by comparing the pattern of gene expression overtime in test cell populations derived from the subject, the prognosis of the subject can be assessed.

The reference profile includes primarily noncancerous or cancerous cells. A reference profile which includes primarily noncancerous cells is a non-cancer reference profile. A reference profile which includes primarily cancerous cells is a cancer reference profile. In some embodiments the cancer reference profile includes primarily disseminated cancerous cells. When the reference profile includes primarily noncancerous cells, an increase of expression of TSCX nucleic acids in the test cell population, indicates less favorable prognosis. Conversely, when the reference profile includes primarily cancerous cells, a decrease of expression of TSCX nucleic acids in the test cell population, indicates more favorable prognosis.

Pharmaceutical Compositions

In another aspect the invention includes pharmaceutical, or therapeutic, compositions containing one or more therapeutic compounds described herein. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity.

TSCX Nucleic Acids

Also provided in the invention are novel nucleic acid comprising a nucleic acid sequence selected from the group consisting of TSC: 1-8, 10-12, and 15-25 (SEQ ID NO: 1-22) or its complement, as well as vectors and cells including these nucleic acids.

Thus, one aspect of the invention pertains to isolated TSCX nucleic acid molecules that encode TSCX proteins or biologically active portions thereof. Also included are nucleic acid fragments sufficient for use as hybridization probes to identify TSCX-encoding nucleic acids (e.g., TSCX mRNA) and fragments for use as polymerase chain reaction (PCR) primers for the amplification or mutation of TSCX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt) or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TSCX nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of any of TSC: 1-8, 10-12, and 15-25, or a complement of any of these nucleotide sequences, can be isolated using standard molecular biology techniques and the sequence information provided herein. Using all or a portion of these nucleic acid sequences as a hybridization probe, TSCX nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TSCX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt and as many as 50 nt, preferably about 15 nt to 30 nt. They may be chemically synthesized and may be used as probes.

In another embodiment, an isolated nucleic acid molecule of the invention comprises a nucleic acid molecule that is a complement of the nucleotide sequence shown in TSCX::1-7, 10-13, 19-34, 45-53, 58-85, 111-113, 120, 130, 132-134 and 138. In another embodiment, an isolated nucleic acid molecule of the invention comprises a nucleic acid molecule that is a complement of the nucleotide sequence shown in any of these sequences, or a portion of any of these nucleotide sequences. A nucleic acid molecule that is complementary to the nucleotide sequence shown in TSC: 1-8, 10-12, and 15-25 is one that is sufficiently complementary to the nucleotide sequence shown, such that it can hydrogen bond with little or no mismatches to the nucleotide sequences shown, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of TSC: 1-8, 10-12, and 15-25 e.g., a fragment that can be used as a probe or primer or a fragment encoding a biologically active portion of TSCX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which in incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a TSCX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a TSCX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding a human TSCX protein. Homologous nucleic acid sequences include those nucleic acid sequences that encode conservative amino acid substitutions (see below) in a TSCX polypeptide, as well as a polypeptide having a TSCX activity. A homologous amino acid sequence does not encode the amino acid sequence of a human TSCX polypeptide.

The nucleotide sequence determined from the cloning of human TSCX genes allows for the generation of probes and primers designed for use in identifying and/or cloning TSCX homologues in other cell types, e.g., from other tissues, as well as TSCX homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of a nucleic acid comprising a TSCX sequence, or an anti-sense strand nucleotide sequence of a nucleic acid comprising a TSCX sequence, or of a naturally occurring mutant of these sequences.

Probes based on human TSCX nucleotide sequences can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a TSCX protein, such as by measuring a level of a TSCX-encoding nucleic acid in a sample of cells from a subject e.g., detecting TSCX mRNA levels or determining whether a genomic TSCX gene has been mutated or deleted.

"A polypeptide having a biologically active portion of TSCX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of TSCX" can be prepared by isolating a portion of TSC: 1-8, 10-12, and 15-25, that encodes a polypeptide having a TSCX biological activity, expressing the encoded portion of TSCX protein (e.g., by recombinant expression in vitro) and assessing the activity of the encoded portion of TSCX. For example, a nucleic acid fragment encoding a biologically active portion of a TSCX polypeptide can optionally include an ATP-binding domain. In another embodiment, a nucleic acid fragment encoding a biologically active portion of TSCX includes one or more regions.

TSCX Variants

The invention further encompasses nucleic acid molecules that differ from the disclosed or referenced TSCX nucleotide sequences due to degeneracy of the genetic code. These nucleic acids thus encode the same TSCX protein as that encoded by nucleotide sequence comprising a TSCX nucleic acid as shown in, e.g., TSC: 1-8, 10-12, and 15-25

In addition to the rat TSCX nucleotide sequence shown in TSC: 1-8, 10-12, and 15-25, it will be appreciated by those skilled in the art that DNA sequence polymorphisms that lead to changes in the amino acid sequences of a TSCX polypeptide may exist within a population (e.g., the human population). Such genetic polymorphism in the TSCX gene may exist among individuals within a population due to natural allelic variation. As used herein, the terms "gene" and "recombinant gene" refer to nucleic acid molecules comprising an open reading frame encoding a TSCX protein, preferably a mammalian TSCX protein. Such natural allelic variations can typically result in 1-5% variance in the nucleotide sequence of the TSCX gene. Any and all such nucleotide variations and resulting amino acid polymorphisms in TSCX that are the result of natural allelic variation and that do not alter the functional activity of TSCX are intended to be within the scope of the invention.

Moreover, nucleic acid molecules encoding TSCX proteins from other species, and thus that have a nucleotide sequence that differs from the human sequence of TSC: 1-8, 10-12, and 15-25, are intended to be within the scope of the invention. Nucleic acid molecules corresponding to natural allelic variants and homologues of the TSCX DNAs of the invention can be isolated based on their homology to the human TSCX nucleic acids disclosed herein using the human cDNAs, or a portion thereof, as a hybridization probe according to standard hybridization techniques under stringent hybridization conditions. For example, a soluble human TSCX DNA can be isolated based on its homology to human membrane-bound TSCX. Likewise, a membrane-bound human TSCX DNA can be isolated based on its homology to soluble human TSCX.

Accordingly, in another embodiment, an isolated nucleic acid molecule of the invention is at least 6 nucleotides in length and hybridizes under stringent conditions to the nucleic acid molecule comprising the nucleotide sequence of TSC: 1-8, 10-12, and 15-25. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding TSCX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of TSC: 1-8, 10-12, and 15-25 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of TSC: 1-8, 10-12, and 15-25 or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, et al. (eds.), NY.

In a third embodiment, a nucleic acid that is hybridizable to the nucleic acid molecule comprising the nucleotide sequence of TSC: 1-8, 10-12, and 15-25 or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo et al., 1981, *Proc Natl Acad Sci USA* 78: 6789-6792.

Conservative Mutations

In addition to naturally-occurring allelic variants of the TSCX sequence that may exist in the population, the skilled artisan will further appreciate that changes can be introduced into an TSCX nucleic acid or directly into an TSCX polypeptide sequence without altering the functional ability of the TSCX protein. In some embodiments, the nucleotide sequence of TSC: 1-8, 10-12, and 15-25 will be altered, thereby leading to changes in the amino acid sequence of the encoded TSCX protein. For example, nucleotide substitutions that result in amino acid substitutions at various "non-essential" amino acid residues can be made in the sequence of TSC: 1-8, 10-12, and 15-25. A "non-essential" amino acid residue is a residue that can be altered from the wild-type sequence of TSCX without altering the biological activity, whereas an "essential" amino acid residue is required for biological activity. For example, amino acid residues that are conserved among the TSCX proteins of the present invention, are predicted to be particularly unamenable to alteration.

In addition, amino acid residues that are conserved among family members of the TSCX proteins of the present invention, are also predicted to be particularly unamenable to alteration. As such, these conserved domains are not likely to be amenable to mutation. Other amino acid residues, however, (e.g., those that are not conserved or only semi-conserved among members of the TSCX proteins) may not be essential for activity and thus are likely to be amenable to alteration.

Another aspect of the invention pertains to nucleic acid molecules encoding TSCX proteins that contain changes in amino acid residues that are not essential for activity. Such TSCX proteins differ in amino acid sequence from the amino acid sequences of polypeptides encoded by nucleic acids containing TSC: 1-8, 10-12, and 15-25, yet retain biological activity. In one embodiment, the isolated nucleic acid molecule comprises a nucleotide sequence encoding a protein, wherein the protein comprises an amino acid sequence at least about 45% homologous, more preferably 60%, and still more preferably at least about 70%, 80%, 90%, 95%, 98%, and most preferably at least about 99% homologous to the amino acid sequence of the amino acid sequences of polypeptides encoded by nucleic acids comprising TSC: 1-8, 10-12, and 15-25.

An isolated nucleic acid molecule encoding a TSCX protein homologous to can be created by introducing one or more nucleotide substitutions, additions or deletions into the nucleotide sequence of a nucleic acid comprising TSC: 1-8, 10-12, and 15-25, such that one or more amino acid substitutions, additions or deletions are introduced into the encoded protein.

Mutations can be introduced into a nucleic acid comprising TSC: 1-8, 10-12, and 15-25 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in TSCX is replaced with another amino acid residue from the same side chain family. Alternatively, in another embodiment, mutations can be introduced randomly along all or part of a TSCX coding sequence, such as by saturation mutagenesis, and the resultant mutants can be screened for TSCX biological activity to identify mutants that retain activity. Following mutagenesis of the nucleic acid, the encoded protein can be expressed by any recombinant technology known in the art and the activity of the protein can be determined.

In one embodiment, a mutant TSCX protein can be assayed for (1) the ability to form protein:protein interactions with other TSCX proteins, other cell-surface proteins, or biologically active portions thereof, (2) complex formation between a mutant TSCX protein and a TSCX ligand; (3) the ability of a mutant TSCX protein to bind to an intracellular target protein or biologically active portion thereof; (e.g., avidin proteins); (4) the ability to bind ATP; or (5) the ability to specifically bind a TSCX protein antibody.

In other specific embodiments, the nucleic acid is RNA or DNA. The fragment or the fragment of the complementary polynucleotide sequence is between about 10 and about 100 nucleotides in length, e.g., between about 10 and about 90 nucleotides in length, or about 10 and about 75 nucleotides in length, about 10 and about 50 bases in length, about 10 and about 40 bases in length, or about 15 and about 30 bases in length.

Antisense

Another aspect of the invention pertains to isolated antisense nucleic acid molecules that are hybridizable to or complementary to the nucleic acid molecule comprising the nucleotide sequence of a TSCX sequence or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire TSCX coding strand, or to only a portion thereof. Nucleic acid molecules encoding fragments, homologs, derivatives and analogs of a TSCX protein, or antisense nucleic acids complementary to a nucleic acid comprising a TSCX nucleic acid sequence are additionally provided.

In one embodiment, an antisense nucleic acid molecule is antisense to a "coding region" of the coding strand of a nucleotide sequence encoding TSCX. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding TSCX. The term "noncoding region" refers to 5' and 3' sequences which flank the coding region that are not translated into amino acids (i.e., also referred to as 5' and 3' untranslated regions).

Given the coding strand sequences encoding TSCX disclosed herein, antisense nucleic acids of the invention can be designed according to the rules of Watson and Crick or Hoogsteen base pairing. The antisense nucleic acid molecule can be complementary to the entire coding region of TSCX mRNA, but more preferably is an oligonucleotide that is antisense to only a portion of the coding or noncoding region of TSCX mRNA. For example, the antisense oligonucleotide can be complementary to the region surrounding the translation start site of TSCX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a TSCX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625-6641). The antisense nucleic acid molecule can also comprise a 2'-o-methylribonucleotide (Inoue et al. (1987) *Nucleic Acids Res* 15: 6131-6148) or a chimeric RNA-DNA analogue (Inoue et al. (1987) *FEBS Lett* 215: 327-330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave TSCX mRNA transcripts to thereby inhibit translation of TSCX mRNA. A ribozyme having specificity for a TSCX-encoding nucleic acid can be designed based upon the nucleotide sequence of a TSCX DNA disclosed herein. For example, a derivative of a Tetrahymena L-19 IVS RNA can be constructed in which the nucleotide sequence of the active site is complementary to the nucleotide sequence to be cleaved in a TSCX-encoding mRNA. See, e.g., Cech et al. U.S. Pat. No. 4,987,071; and Cech et al. U.S. Pat. No. 5,116, 742. Alternatively, TSCX mRNA can be used to select a catalytic RNA having a specific ribonuclease activity from a pool of RNA molecules. See, e.g., Bartel et al., (1993) *Science* 261:1411-1418.

Alternatively, TSCX gene expression can be inhibited by targeting nucleotide sequences complementary to the regulatory region of a TSCX nucleic acid (e.g., the TSCX promoter and/or enhancers) to form triple helical structures that prevent transcription of the TSCX gene in target cells. See generally, Helene. (1991) *Anticancer Drug Des*. 6: 569-84; Helene. et al. (1992) *Ann. N.Y. Acad. Sci*. 660:27-36; and Maher (1992) *Bioassays* 14: 807-15.

In various embodiments, the nucleic acids of TSCX can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670-675.

PNAs of TSCX can be used in therapeutic and diagnostic applications. For example, PNAs can be used as antisense or antigene agents for sequence-specific modulation of gene expression by, e.g., inducing transcription or translation arrest or inhibiting replication. PNAs of TSCX can also be used, e.g., in the analysis of single base pair mutations in a gene by, e.g., PNA directed PCR clamping; as artificial restriction enzymes when used in combination with other enzymes, e.g., 51 nucleases (Hyrup B. (1996) above); or as probes or primers for DNA sequence and hybridization (Hyrup et al. (1996), above; Perry-O'Keefe (1996), above).

In another embodiment, PNAs of TSCX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of TSCX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357-63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973-88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119-11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553-6556; Lemaitre et al., 1987, *Proc. Natl. Acad. Sci.* 84:648-652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958-976) or intercalating agents. (See, e.g., Zon, 1988, *Pharm. Res.* 5: 539-549). To this end, the oligonucleotide may be conjugated to another molecule, e.g., a peptide, a hybridization triggered cross-linking agent, a transport agent, a hybridization-triggered cleavage agent, etc.

TSCX Polypeptides

One aspect of the invention pertains to isolated TSCX proteins, and biologically active portions thereof, or derivatives, fragments, analogs or homologs thereof. Also provided are polypeptide fragments suitable for use as immunogens to raise anti-TSCX antibodies. In one embodiment, native TSCX proteins can be isolated from cells or tissue sources by an appropriate purification scheme using standard protein purification techniques. In another embodiment, TSCX proteins are produced by recombinant DNA techniques. Alternative to recombinant expression, a TSCX protein or polypeptide can be synthesized chemically using standard peptide synthesis techniques.

An "isolated" or "purified" protein or biologically active portion thereof is substantially free of cellular material or other contaminating proteins from the cell or tissue source from which the TSCX protein is derived, or substantially free from chemical precursors or other chemicals when chemically synthesized. The language "substantially free of cellular material" includes preparations of TSCX protein in which the protein is separated from cellular components of the cells from which it is isolated or recombinantly produced. In one embodiment, the language "substantially free of cellular material" includes preparations of TSCX protein having less than about 30% (by dry weight) of non-TSCX protein (also referred to herein as a "contaminating protein"), more preferably less than about 20% of non-TSCX protein, still more preferably less than about 10% of non-TSCX protein, and most preferably less than about 5% non-TSCX protein. When the TSCX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of TSCX protein in which the protein is separated from chemical precursors or other chemicals that are involved in the synthesis of the protein. In one embodiment, the language "substantially free of chemical precursors or other chemicals" includes preparations of TSCX protein having less than about 30% (by dry weight) of chemical precursors or non-TSCX chemicals, more preferably less than about 20% chemical precursors or non-TSCX chemicals, still more preferably less than about 10% chemical precursors or non-TSCX chemicals, and most preferably less than about 5% chemical precursors or non-TSCX chemicals.

Biologically active portions of a TSCX protein include peptides comprising amino acid sequences sufficiently homologous to or derived from the amino acid sequence of the TSCX protein, e.g., the amino acid sequence encoded by a nucleic acid comprising TSCX 1-20 that include fewer amino acids than the full length TSCX proteins, and exhibit at least one activity of a TSCX protein. Typically, biologically active portions comprise a domain or motif with at least one activity of the TSCX protein. A biologically active portion of a TSCX protein can be a polypeptide which is, for example, 10, 25, 50, 100 or more amino acids in length.

A biologically active portion of a TSCX protein of the present invention may contain at least one of the above-identified domains conserved between the TSCX proteins. An alternative biologically active portion of a TSCX protein may contain at least two of the above-identified domains. Another biologically active portion of a TSCX protein may contain at least three of the above-identified domains. Yet another biologically active portion of a TSCX protein of the present invention may contain at least four of the above-identified domains.

Moreover, other biologically active portions, in which other regions of the protein are deleted, can be prepared by recombinant techniques and evaluated for one or more of the functional activities of a native TSCX protein.

In some embodiments, the TSCX protein is substantially homologous to one of these TSCX proteins and retains its the functional activity, yet differs in amino acid sequence due to natural allelic variation or mutagenesis, as described in detail below.

In specific embodiments, the invention includes an isolated polypeptide comprising an amino acid sequence that is 80% or more identical to the sequence of a polypeptide whose expression is modulated in a mammal to which TSCXic agent is administered.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See *Needleman and Wunsch* 1970 *J Mol Biol* 48: 443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of a DNA sequence comprising TSCX::1-7, 10-13, 19-34, 45-53, 58-85, 111-113, 120, 130, 132-134 and 138.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides TSCX chimeric or fusion proteins. As used herein, an TSCX "chimeric protein" or "fusion protein" comprises an TSCX polypeptide operatively linked to a non-TSCX polypeptide. A "TSCX polypeptide" refers to a polypeptide having an amino acid sequence corresponding to TSCX, whereas a "non-TSCX polypeptide" refers to a polypeptide having an amino acid sequence corresponding to a protein that is not substantially homologous to the TSCX protein, e.g., a protein that is different from the TSCX protein and that is derived from the same or a different organism. Within an TSCX fusion protein the TSCX polypeptide can correspond to all or a portion of an TSCX protein. In one embodiment, an TSCX fusion protein comprises at least one biologically active portion of an TSCX protein. In another embodiment, an TSCX fusion protein comprises at least two biologically active portions of an TSCX protein. In yet another embodiment, an TSCX fusion protein comprises at least three biologically active portions of an TSCX protein. Within the fusion protein, the term "operatively linked" is intended to indicate that the TSCX polypeptide and the non-TSCX polypeptide are fused in-frame to each other. The non-TSCX polypeptide can be fused to the N-terminus or C-terminus of the TSCX polypeptide.

For example, in one embodiment an TSCX fusion protein comprises an TSCX domain operably linked to the extracellular domain of a second protein. Such fusion proteins can be further utilized in screening assays for compounds which modulate TSCX activity (such assays are described in detail below).

In yet another embodiment, the fusion protein is a GST-TSCX fusion protein in which the TSCX sequences are fused to the C-terminus of the GST (i.e., glutathione S-transferase) sequences. Such fusion proteins can facilitate the purification of recombinant TSCX.

In another embodiment, the fusion protein is an TSCX protein containing a heterologous signal sequence at its N-terminus. For example, a native TSCX signal sequence can be removed and replaced with a signal sequence from another protein. In certain host cells (e.g., mammalian host cells), expression and/or secretion of TSCX can be increased through use of a heterologous signal sequence.

In yet another embodiment, the fusion protein is an TSCX-immunoglobulin fusion protein in which the TSCX sequences comprising one or more domains are fused to sequences derived from a member of the immunoglobulin protein family. The TSCX-immunoglobulin fusion proteins of the invention can be incorporated into pharmaceutical compositions and administered to a subject to inhibit an interaction between a TSCX ligand and a TSCX protein on the surface of a cell, to thereby suppress TSCX-mediated signal transduction in vivo. The TSCX-immunoglobulin fusion proteins can be used to affect the bioavailability of an TSCX cognate ligand Inhibition of the TSCX ligand/TSCX interaction may be useful therapeutically for both the treatments of proliferative and differentiative disorders, as well as modulating (e.g. promoting or inhibiting) cell survival. Moreover, the TSCX-immunoglobulin fusion proteins of the invention can be used as immunogens to produce anti-TSCX antibodies in a subject, to purify TSCX ligands, and in screening assays to identify molecules that inhibit the interaction of TSCX with a TSCX ligand.

An TSCX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An TSCX-encoding nucleic acid can be cloned into such an expression vector such that the fusion moiety is linked in-frame to the TSCX protein.

TSCX Agonists and Antagonists

The present invention also pertains to variants of the TSCX proteins that function as either TSCX agonists (mimetics) or as TSCX antagonists. Variants of the TSCX protein can be generated by mutagenesis, e.g., discrete point mutation or truncation of the TSCX protein. An agonist of the TSCX protein can retain substantially the same, or a subset of, the biological activities of the naturally occurring form of the TSCX protein. An antagonist of the TSCX protein can inhibit one or more of the activities of the naturally occurring form of the TSCX protein by, for example, competitively binding to a downstream or upstream member of a cellular signaling cascade which includes the TSCX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the TSCX proteins.

Variants of the TSCX protein that function as either TSCX agonists (mimetics) or as TSCX antagonists can be identified by screening combinatorial libraries of mutants, e.g., truncation mutants, of the TSCX protein for TSCX protein agonist or antagonist activity. In one embodiment, a variegated library of TSCX variants is generated by combinatorial mutagenesis at the nucleic acid level and is encoded by a variegated gene library. A variegated library of TSCX variants can be produced by, for example, enzymatically ligating a mixture of synthetic oligonucleotides into gene sequences such that a degenerate set of potential TSCX sequences is expressible as individual polypeptides, or alternatively, as a set of larger fusion proteins (e.g., for phage display) containing the set of TSCX sequences therein. There are a variety of methods which can be used to produce libraries of potential TSCX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TSCX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the TSCX protein coding sequence can be used to generate a variegated population of TSCX fragments for screening and subsequent selection of variants of an TSCX protein. In one embodiment, a library of coding sequence fragments can be generated by treating a double stranded PCR fragment of a TSCX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the TSCX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TSCX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TSCX variants (Arkin and Yourvan (1992) PNAS 89:7811-7815; Delgrave et al. (1993) Protein Engineering 6:327-331).

Anti-TSCX Antibodies

An isolated TSCX protein, or a portion or fragment thereof, can be used as an immunogen to generate antibodies that bind TSCX using standard techniques for polyclonal and monoclonal antibody preparation. The full-length TSCX protein can be used or, alternatively, the invention provides antigenic peptide fragments of TSCX for use as immunogens. The antigenic peptide of TSCX comprises at least 8 amino acid residues of the amino acid sequence encoded by a nucleic acid comprising the nucleic acid sequence shown in TSC: 1-8, 10-12, and 15-25 and encompasses an epitope of TSCX such that an antibody raised against the peptide forms a specific immune complex with TSCX. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of TSCX that are located on the surface of the protein, e.g., hydrophilic regions. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety.

TSCX polypeptides or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen. Such antibodies include, but are not limited to, polyclonal, monoclonal, chimeric, single chain, $F_{ab}$ and $F_{(ab')2}$ fragments, and an $F_{ab}$ expression library. Various procedures known within the art may be used for the production of polyclonal or monoclonal antibodies to an TSCX protein sequence, or derivatives, fragments, analogs or homologs thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed TSCX protein or a chemically synthesized TSCX polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against TSCX can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of TSCX. A monoclonal antibody composition thus typically displays a single binding affinity for a particular TSCX protein with which it immunoreacts. For preparation of monoclonal antibodies directed towards a particular TSCX protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495-497); the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

According to the invention, techniques can be adapted for the production of single-chain antibodies specific to a TSCX protein (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a TSCX protein or derivatives, fragments, analogs or homologs thereof. Non-human antibodies can be "humanized" by techniques well known in the art. See e.g., U.S. Pat. No. 5,225,539. Antibody fragments that contain the idiotypes to a TSCX protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii)

an F$_{ab}$ fragment generated by the treatment of the antibody molecule with papain and a reducing agent and (iv) F$_v$ fragments.

Additionally, recombinant anti-TSCX antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., (1988) *Science* 240:1041-1043; Liu et al. (1987) *PNAS* 84:3439-3443; Liu et al. (1987) *J Immunol.* 139:3521-3526; Sun et al. (1987) *PNAS* 84:214-218; Nishimura et al. (1987) *Cancer Res* 47:999-1005; Wood et al. (1985) *Nature* 314:446-449; Shaw et al. (1988) *J Natl Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J Immunol* 141:4053-4060.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a TSCX protein is facilitated by generation of hybridomas that bind to the fragment of a TSCX protein possessing such a domain. Antibodies that are specific for one or more domains within a TSCX protein, e.g., domains spanning the above-identified conserved regions of TSCX family proteins, or derivatives, fragments, analogs or homologs thereof, are also provided herein.

Anti-TSCX antibodies may be used in methods known within the art relating to the localization and/or quantitation of a TSCX protein (e.g., for use in measuring levels of the TSCX protein within appropriate physiological samples, for use in diagnostic methods, for use in imaging the protein, and the like). In a given embodiment, antibodies for TSCX proteins, or derivatives, fragments, analogs or homologs thereof, that contain the antibody derived binding domain, are utilized as pharmacologically-active compounds [hereinafter "Therapeutics"].

An anti-TSCX antibody (e.g., monoclonal antibody) can be used to isolate TSCX by standard techniques, such as affinity chromatography or immunoprecipitation. An anti-TSCX antibody can facilitate the purification of natural TSCX from cells and of recombinantly produced TSCX expressed in host cells. Moreover, an anti-TSCX antibody can be used to detect TSCX protein (e.g., in a cellular lysate or cell supernatant) in order to evaluate the abundance and pattern of expression of the TSCX protein. Anti-TSCX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

TSCX Recombinant Expression Vectors and Host Cells

Another aspect of the invention pertains to vectors, preferably expression vectors, containing a nucleic acid encoding TSCX protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TSCX proteins, mutant forms of TSCX, fusion proteins, etc.).

The recombinant expression vectors of the invention can be designed for expression of TSCX in prokaryotic or eukaryotic cells. For example, TSCX can be expressed in bacterial cells such as *E. coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:211:1-7, 10-13, 19-34, 45-53, 58-85, 111-113, 120, 130, 132-134 and 13518). Such alteration of nucleic acid sequences of the invention can be carried out by standard DNA synthesis techniques.

In another embodiment, the TSCX expression vector is a yeast expression vector. Examples of vectors for expression in yeast *S. cerevisiae* include pYepSec1 (Baldari, et al., (1987) *EMBO J* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, TSCX can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268-277), lymphoid-specific promoters (Calame and Eaton (1988) *Adv Immunol* 43:235-275), in particular promoters of T cell receptors (Winoto and Baltimore (1989) *EMBO J* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374-379) and the α-fetoprotein promoter (Campes and Tilghman (1989) *Genes Dev* 3:537-546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to TSCX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TSCX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding TSCX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an TSCX protein. Accordingly, the invention further provides methods for producing TSCX protein using the host cells of the invention. In one embodiment, the method comprises culturing the host cell of invention (into which a recombinant expression vector encoding TSCX has been introduced) in a suitable medium such that TSCX protein is produced. In another embodiment, the method further comprises isolating TSCX from the medium or the host cell.

Kits and Nucleic Acid Collections for Identifying TSCX Nucleic Acids

In another aspect, the invention provides a kit useful for examining TSCXicity of agents. The kit can include nucleic acids that detect two or more TSCX sequences. In preferred embodiments, the kit includes reagents which detect 3, 4, 5, 6, 8, 10, 12, 15, 20, 25, 50, 100 or all of the TSCX nucleic acid sequences.

The invention also includes an isolated plurality of sequences which can identify one or more TSCX responsive nucleic acid sequences.

The kit or plurality may include, e.g., sequence homologous to TSCX nucleic acid sequences, or sequences which can specifically identify one or more TSCX nucleic acid sequences.

EXAMPLES

Example 1

Expression Analysis of Antileukoprotease in Various Tissues

The quantitative expression of NMB (GenBank™ Accession No: AJ251685; Table 1; NMB or TSC122, listed in Table 1 on page 10) was assessed using microtiter plates containing RNA samples from a variety of normal and pathology-derived cells, cell lines and tissues using real time quantitative PCR(RTQ PCR; TAQMAN®). RTQ PCR was performed on a Perkin-Elmer Biosystems ABI PRISM® 7700 Sequence Detection System. Various collections of samples are assembled on the plates, and referred to as Panel 1 (containing cells and cell lines from normal and cancer sources), and Panel 2 (containing samples derived from tissues, in particular from surgical samples, from normal and cancer sources). The amino acid sequence of the NMB polypeptide is MESLCGVLGFLLLAAGLPLQAAKRFRDV-LGHEQYPDHMREHNQLRGWSSDENEWD-EHLYPVWRRGDGRWKDSWEGGRVQAV-LTSDSPALVGSNITFVVNLVFRCQKEDANGNIVYEKN CRNDLGLTSDLHVYNWTAGADDGD-WEDGTSRSQHLRFPDRRPFPRPHG-WKKWSFVYVFHTLGQYFQKLGRCSARVS-INTVNLTAGPQVMEVTVFRRYGRAYIPISKVKDVYVI TDQIPVFVTMSQKNDRNLSDEIFL-RDLPIVFDVLIHDPSHFLNDSAISYKWN-FGDNTGLFVSNNHTLNHTYVLNGTFNLN-LTVQTAVPGPCPPPSPSTPPSPSTPPLPSPSPLPTLSTPSP SLMPTGYKSMELSDISNENCRINRYGY-FRATITIVEGILEVSIMQIADVPMPTPQ-PANSLMDFTVTCKGATPMEACTIIS-DPTCQIAQNRVCSPVAVDGLCLLSVRRAFNGSGTYCV NFTLGDDASLALTSTLISIPGKDPDSPL-RAVNGVLISIGCLAVLVTMVTILLYKKH-KAYKPIGNCPRNTVKGKGLSV-LLSHAKAPFFRGDQEKDPLLQDKPRTL (SEQ ID NO:27). The nucleotide sequence encoding this protein is (SEQ ID NO: 26)

```
atcgcaggaggccgacactgtgactcctggtggatcgggactggggagtcagagtcaagccctgactggttgcaggcgctcggagtcagc atggaaagtctctgcggggtcctgggatttctgctgctggctgcaggactgcctctccaggctgccaagcgatttcgtgatgtgctgggccatg aacagtatcccgatcacatgagagagcacaaccaattacgtggctggtcttcggatgaaaatgaatgggatgaacacctgtatccagtgtgga ggaggggagacggcaggtggaaggactcctgggaaggaggccgtgtgcaggcagtcctgaccagtgactcaccggctctggtgggttcc aatatcacttttgtggtgaacctggtgttccccagatgccagaaggaagatgctaatggcaatatcgtctatgagaagaactgcaggaatgattt gggactgacatctgacctgcatgtctacaactggactgcaggggcagatgatggtgactgggaagatggcaccagccgaagccagcatctc aggttcccggacaggaggcccttccctcgcccccatggatggaagaaatggagctttgtctacgtctttcacacacttggccagtatttccaaa aactgggtcggtgttcagcacgggtttctataaacacagtcaacttgacagctggccctcaggtcatggaagtgactgtctttcgaagatacgg ccgggcatacattcccatctcgaaggtgaaagatgtgtatgtgataacagatcagatccctgtattcgtgaccatgtcccagaagaatgacagg
```

-continued

```
aacttgtctgatgagatcttcctcagagacctccccatcgtcttcgatgtcctcattcatgatcccagccacttcctcaacgactctgccatttccta caagtggaactttggggacaacactggcctgtttgtctccaacaatcacactttgaatcacacttatgtgctcaatggaaccttcaaccttaacct caccgtgcaaactgcagtgccccgggccatgcctccccttcgccttcgactccgccttcaccttcaactccgcccttaccttcgccctcacctt tgcccacattatcaacacctagcccctctttaatgcctactggttacaaatccatggagctgagtgacatttccaatgaaaactgccgaataaac agatatggctacttcagagccaccatcacaattgtagaggggatcctggaagtcagcatcatgcagatagcagatgtccccatgcccacacc gcagcctgccaactccctgatggacttcactgtgacctgcaaaggggccaccccatggaagcctgtacgatcatctccgacccacctgcc agatcgcccagaacccgggtctgcagccctgtggctgtggatgggctgtgcctgctgtctgtgagaagagccttcaatgggtctggcacctact gtgtgaatttcactctgggagatgatgcaagcctggcctcaccagcaccctgatctctatccctggcaaagacccagactcccctctgagag cagtgaatggtgtcctgatctccatcggctgcctggctgtgcttgtcaccatggttaccatcttgctgtacaaaaaacacaaggcgtacaagcc aataggaaactgccccaggaacacggtcaagggcaagggcctgagtgttctcctcagtcacgcgaaagcccgttcttccgaggagacca ggagaaggatccattgctccaggacaagccaaggacactctaagtctttggccttccctctgaccaggaacccactcttctgtgcatgtatgtg agctgtgcagaagtatgtggctgggaactgttgttctctaaggattattgtaaaatgtatatcgtggcttagggagtgtggttaaatagcattttag agaagacatgggaagacttagtgtttcttcccatctgtattgtggtttttacactgttcgtggggtggacacgctgtgtctgaagggggagtggg gtcactgctacttaaggtcctaggttaactggggagataccacagatgccttcagctttccacataacatgggcatgaacccagctaatcacc acctgaaggccatgcttcatctgccttccaactcactgagcatgcctgagctcctgacaaaattataatgggcccgggcttttgtgtatgggtgc cgtgtggtgtacatattctactcattaaaaaaggcagtctaaaaaaaaaaaaaaaaaa (GenBank™ Accession No: AJ251685).
```

First, the RNA samples were normalized to constitutively expressed genes such as β-actin and GAPDH. RNA (~50 ng total or ~1 ng polyA+) was converted to cDNA using the TAQMAN® Reverse Transcription Reagents Kit (PE Biosystems, Foster City, Calif.; Catalog No. N808-0234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; Catalog Nos. 4310881E and 4310884E, respectively) and TAQMAN® universal PCR Master Mix (PE Biosystems; Catalog No. 4304447) according to the manufacturer's protocol. Reactions were performed in 25 ul using the following parameters: 2 min. at 50° C.; 10 min. at 95° C.; 15 sec. at 95° C./1 min. at 60° C. (40 cycles). Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their β-actin/GAPDH average CT values.

Normalized RNA (5 ul) was converted to cDNA and analyzed via TAQMAN® using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58°-60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (a probe specific for the target clone and another gene-specific probe multiplexed with the target probe) were set up using 1× TaqMan™ PCR Master Mix for the PE Biosystems 7700, with 5 mM MgC12, dNTPs (dA, G, C, U at 1:1:1:2 ratios), 0.25 U/ml AmpliTaq Gold™ (PE Biosystems), and 0.4 U/μl RNase inhibitor, and 0.25 U/μl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

In the results for Panel 1, the following abbreviations are used:
ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma.
Panel 2

The plates for Panel 2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDRI). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologists at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table 4). In addition, RNA and cDNA samples were obtained from various human tissues derived from autopsies performed on elderly people or sudden death victims (accidents, etc.). These tissue were ascertained to be free of disease and were purchased from various commercial sources such as Clontech (Palo Alto, Calif.), Research Genetics, and Invitrogen.

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

The TaqMan™ expression profiles of NMB were generated using a specific gene probes and primer set (Ag 817) as shown below:

Ag 817 forward: 5'-TCAATGGAACCTTCAGCCTTA-3' [SEQ ID NO.: 23] ProbeTET: 5'-CTCACTGTGAAAGCTG-CAGCACCAG-3'-TAMRA [SEQ ID NO.: 24] Reverse: 5'-GAAGGGGTGGGTTTTGAAG-3' [SEQ ID NO.: 25 ].

The results shown in Table 2 (see below) relate to 41 normal human tissues and 55 human cancer cell lines and demonstrate the high expression of NMB in melanomas cell lines and overexpression in the breast cancer cell line MDA-N. The results shown in Table 3 (see below) relate to additional tumor tissues, many of which are matched with normal adjacent tissue (NAT), as defined by the operating surgeon that obtained the samples. It reveals that NMB is overexpressed in 9/9 kidney tumors compared either with normal kidney or NAT. This analysis corroborates the GeneCalling™ results which originally identified the expression of NMB that NMB is also overexpressed in some of the lung carcinoma tissues compared with NATs and 2 melanoma metastasis compared with NAT.

NCI's CGAP Sage analysis indicates that NMB is expressed in several glioblastoma (H392, pooled GBM, GBMH1110), and in 1 malignant breast tumor (SKBR3), in accordance with panel 1 TaqMan analysis. NCI data for EST expression, called "body map", reveals that NMB is expressed in Schwann cells, in adenocarcinoma and s. cell carcinoma.

Based on NMB's gene expression profile and its homology with pMEL17, it is anticipated that for a subset of human tumors including renal cell carcinomas, lung carcinomas, melanomas and CNS cancers, successful targeting of NMB using a monoclonal antibody will have an inhibitory effect on tumor growth, matrix invasion and metastatic dissemination. Furthermore, targeting of NMB will have a therapeutic effect on the TSC disease.

Furthermore, in consideration of NMB potential enzymatic activity, NMB could be used as a target for screening a small molecule drug.

In summary, these results demonstate the relevance of NMB as a therapeutic target for the treatment of TSC is strengthened by its expression/overexpression in several tissues that are affected in TSC.

TABLE 2

Taq Man results for PANEL 1

| Tissue Name | | Rel. Expr., % 1.2tm958t_ag817 |
|---|---|---|
| Endothelial cells | | 0 |
| Heart (fetal) | | 5.4 |
| Pancreas | | 6 |
| Pancreatic ca. | CAPAN 2 | 0 |
| Adrenal Gland (new lot*) | | 2.7 |
| Thyroid | | 19.3 |
| Salavary gland | | 2.7 |
| Pituitary gland | | 3.7 |
| Brain (fetal) | | 0.8 |
| Brain (whole) | | 2.4 |
| Brain (amygdala) | | 1.6 |
| Brain (cerebellum) | | 0.4 |
| Brain (hippocampus) | | 1.3 |
| Brain (thalamus) | | 1.1 |
| Cerebral Cortex | | 1.2 |
| Spinal cord | | 7.6 |
| CNS ca. (glio/astro) | U87-MG | 27.2 |
| CNS ca. (glio/astro) | U-118-MG | 13.5 |
| CNS ca. (astro) | SW1783 | 0.4 |
| CNS ca.* (neuro; met) | SK-N-AS | 0.7 |
| CNS ca. (astro) | SF-539 | 52.9 |
| CNS ca. (astro) | SNB-75 | 7 |
| CNS ca. (glio) | SNB-19 | 1.3 |
| CNS ca. (glio) | U251 | 4.9 |
| CNS ca. (glio) | SF-295 | 11 |
| Heart | | 17.1 |
| Skeletal Muscle (new lot*) | | 5.7 |
| Bone marrow | | 0.8 |
| Thymus | | 9.9 |
| Spleen | | 5 |
| Lymph node | | 25.7 |
| Colorectal | | 8.2 |
| Stomach | | 5.6 |
| Small intestine | | 8.1 |
| Colon ca. | SW480 | 0 |
| Colon ca.* (SW480 met) | SW620 | 0 |
| Colon ca. | HT29 | 0 |
| Colon ca. | HCT-116 | 0 |
| Colon ca. | CaCo-2 | 0 |
| 83219 CC Well to Mod Diff (ODO3866) | | 2.4 |
| Colon ca. | HCC-2998 | 0.1 |
| Gastric ca.* (liver met) | NCI-N87 | 18.2 |
| Bladder | | 8.1 |
| Trachea | | 7.4 |
| Kidney | | 3.1 |
| Kidney (fetal) | | 1.7 |
| Renal ca. | 786-0 | 0 |
| Renal ca. | A498 | 4.7 |
| Renal ca. | RXF 393 | 1.5 |
| Renal ca. | ACHN | 0 |
| Renal ca. | UO-31 | 1.8 |
| Renal ca. | TK-10 | 0 |
| Liver | | 2.5 |
| Liver (fetal) | | 2.3 |
| Liver ca. (hepatoblast) HepG2 | | 0 |
| Lung | | 21 |

TABLE 3

TaqMan Results for Panel 2

| Tissue Name | Rel. Expr., % 2tm1063t_ag817 |
|---|---|
| Normal Colon GENPAK 061003 | 11.8 |
| 83219 CC Well to Mod Diff (ODO3866) | 0 |
| 83220 CC NAT (ODO3866) | 9.1 |
| 83221 CC Gr.2 rectosigmoid (ODO3868) | 1.4 |
| 83222 CC NAT (ODO3868) | 7.1 |
| 83235 CC Mod Diff (ODO3920) | 1.2 |
| 83236 CC NAT (ODO3920) | 1.2 |
| 83237 CC Gr.2 ascend colon (ODO3921) | 4.8 |
| 83238 CC NAT (ODO3921) | 5.8 |
| 83241 CC from Partial Hepatectomy (ODO4309) | 7.8 |
| 83242 Liver NAT (ODO4309) | 2.9 |
| 87472 Colon mets to lung (OD04451-01) | 14.6 |
| 87473 Lung NAT (OD04451-02) | 19.8 |
| Normal Prostate Clontech A+ 6546-1 | 8.8 |
| 84140 Prostate Cancer (OD04410) | 2.9 |
| 84141 Prostate NAT (OD04410) | 0.7 |
| 87073 Prostate Cancer (OD04720-01) | 1 |
| 87074 Prostate NAT (OD04720-02) | 1.5 |
| Normal Lung GENPAK 061010 | 49.3 |
| 83239 Lung Met to Muscle (ODO4286) | 74.7 |
| 83240 Muscle NAT (ODO4286) | 6.5 |
| 84136 Lung Malignant Cancer (OD03126) | 10.4 |
| 84137 Lung NAT (OD03126) | 4.6 |
| 84871 Lung Cancer (OD04404) | 27.7 |
| 84872 Lung NAT (OD04404) | 7.9 |
| 84875 Lung Cancer (OD04565) | 41.8 |
| 84876 Lung NAT (OD04565)** | 3.8 |
| 85950 Lung Cancer (OD04237-01) | 10.1 |
| 85970 Lung NAT (OD04237-02) | 1.5 |
| 83255 Ocular Mel Met to Liver (ODO4310) | 77.4 |
| 83256 Liver NAT (ODO4310) | 1.8 |
| 84139 Melanoma Mets to Lung (OD04321) | 53.6 |
| 84138 Lung NAT (OD04321) | 5.8 |
| Normal Kidney GENPAK 061008 | 10.1 |
| 83786 Kidney Ca, Nuclear grade 2 (OD04338) | 22.5 |
| 83787 Kidney NAT (OD04338) | 1.3 |
| 83788 Kidney Ca Nuclear grade 1/2 (OD04339) | 17.2 |
| 83789 Kidney NAT (OD04339) | 2 |
| 83790 Kidney Ca, Clear cell type (OD04340) | 11.3 |
| 83791 Kidney NAT (OD04340) | 3.7 |
| 83792 Kidney Ca, Nuclear grade 3 (OD04348) | 12.1 |
| 83793 Kidney NAT (OD04348) | 1.9 |
| 87474 Kidney Cancer (OD04622-01) | 19.6 |
| 87475 Kidney NAT (OD04622-03) | 9 |
| 85973 Kidney Cancer (OD04450-01) | 54.7 |
| 85974 Kidney NAT (OD04450-03) | 2.7 |
| Kidney Cancer Clontech 8120613 | 67.8 |
| Kidney NAT Clontech 8120614 | 5.8 |
| Kidney Cancer Clontech 9010320 | 56.3 |
| Kidney NAT Clontech 9010321 | 7.2 |
| Kidney Cancer Clontech 8120607 | 100 |
| Kidney NAT Clontech 8120608 | 10.2 |
| Normal Uterus GENPAK 061018 | 11.5 |
| Uterus Cancer GENPAK 064011 | 2 |
| Normal Thyroid Clontech A+ 6570-1** | 44.4 |
| Thyroid Cancer GENPAK 064010 | 90.1 |
| Thyroid Cancer INVITROGEN A302152 | 10.9 |
| Thyroid NAT INVITROGEN A302153 | 8.3 |
| Normal Breast GENPAK 061019 | 2.4 |
| 84877 Breast Cancer (OD04566) | 5.5 |
| Breast Cancer Res. Gen. 1024 | 7.1 |
| 85975 Breast Cancer (OD04590-01) | 1.7 |
| 85976 Breast Cancer Mets (OD04590-03) | 2 |
| 87070 Breast Cancer Metastasis (OD04655-05) | 1.6 |
| GENPAK Breast Cancer 064006 | 3.4 |
| Breast Cancer Clontech 9100266 | 11.1 |
| Breast NAT Clontech 9100265 | 7.7 |
| Breast Cancer INVITROGEN A209073 | 11 |
| Breast NAT INVITROGEN A2090734 | 3.2 |
| Normal Liver GENPAK 061009 | 6 |
| Liver Cancer Research Genetics RNA 1026 | 36.3 |
| Liver Cancer Research Genetics RNA 1025 | 4 |
| Paired Liver Cancer Tissue Research Genetics RNA 6004-T | 10.4 |
| Paired Liver Tissue Research Genetics RNA 6004-N | 32.1 |
| Paired Liver Cancer Tissue Research Genetics RNA 6005-T | 44.4 |
| Paired Liver Tissue Research Genetics RNA 6005-N | 40.6 |
| Liver Cancer GENPAK 064003 | 18.4 |
| Normal Bladder GENPAK 061001 | 19.9 |
| Bladder Cancer Research Genetics RNA 1023 | 17 |
| 87071 Bladder Cancer (OD04718-01) | 1.4 |
| 87072 Bladder Normal Adjacent (OD04718-03) | 0.9 |
| Bladder Cancer INVITROGEN A302173 | 43.8 |
| Normal Ovary Res. Gen. | 39.5 |
| Ovarian Cancer GENPAK 064008 | 10.8 |
| 87492 Ovary Cancer (OD04768-07) | 5 |
| 87493 Ovary NAT (OD04768-08) | 6.2 |
| Normal Stomach GENPAK 061017 | 37.4 |
| Gastric Cancer Clontech 9060358** | 7.4 |
| NAT Stomach Clontech 9060359 | 14.6 |
| Gastric Cancer Clontech 9060397 | 40.9 |
| NAT Stomach Clontech 9060396 | 9.9 |
| Gastric Cancer Clontech 9060395 | 20.9 |
| NAT Stomach Clontech 9060394 | 22.2 |
| Gastric Cancer GENPAK 064005 | 8.6 |
| genomic DNA control | 4.5 |
| Chemistry Control | 0.1 |

Example 2

Therapeutic Targeting of CYR61

Based on CYR61's gene expression profile, it is anticipated that for a subset of human tumors including renal cell carcinomas, lung carcinomas, melanomas and CNS cancers, successful targeting of CYR61 using a monoclonal antibody will have an inhibitory effect on tumor growth, matrix invasion and metastatic dissemination. Furthermore, targeting of CYR61 will have a therapeutic effect on the TSC disease.

Example 3

Therapeutic Targeting of NET-7

NET-7 is overexpressed by a breast cancer cell lines and it is regulated by estradiol treatment of a ER positive cell line MCF7. Based on NET-7's gene expression profile, it is anticipated that for a subset of human tumors specifically breast tumors, successful targeting of NET-7 using a monoclonal antibody will have an inhibitory effect on tumor growth, matrix invasion and metastatic dissemination. Furthermore, targeting of NET-7 will have a therapeutic effect on the TSC disease adrenomedullin precursor (and Receptor activity modifying protein 1)

NET-7 has potent and long-lasting vasodilatory effects in several vascular systems. In addition to adrenomedullin, another hypotensive peptide, proadrenomedullin-derived peptide (PAMP), was also found to be processed from the adrenomedullin precursor. PAMP inhibits neural transmission at peripheral sympathetic nerve endings, although adrenomedullin directly dilates vascular smooth muscle. Adrenomedullin might participate in the pathogenesis of hypertension, renal failure and congestive heart failure.

Receptor activity-modifying proteins (RAMPs) are single-transmembrane proteins that transport the calcitonin receptor-like receptor (CRLR) to the cell surface. RAMP 1-transported CRLR is a calcitonin gene-related peptide (CGRP) receptor. RAMP1 is downregulated in NSC. Because of its activities, overexpression of adrenomedullin precursor by TSC patients might explain some of the TSC

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody that immunospecifically binds to an NMB polypeptide encoded by a nucleic acid of SEQ ID NO:26, wherein the NMB polypeptide comprises the amino acid sequence of SEQ ID NO:27.

2. The antibody of claim 1, wherein the antibody is a monoclonal antibody.

3. The antibody of claim 1, wherein the antibody is a human monoclonal antibody.

4. The antibody of claim 1, wherein the antibody is a humanized antibody.

5. A pharmaceutical composition comprising the antibody of claim 1 and a carrier.

* * * * *